US008509902B2

(12) United States Patent (10) Patent No.: US 8,509,902 B2
Cho et al. (45) Date of Patent: Aug. 13, 2013

(54) MEDICAL DEVICE TO PROVIDE BREATHING THERAPY

(75) Inventors: Yong K. Cho, Maple Grove, MN (US); Shaileshkumar Musley, Blaine, MN (US); Avram Scheiner, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 77 days.

(21) Appl. No.: 13/192,914

(22) Filed: Jul. 28, 2011

(65) Prior Publication Data

US 2013/0030488 A1 Jan. 31, 2013

(51) Int. Cl.
*A61N 1/365* (2006.01)
(52) U.S. Cl.
USPC ............................... 607/42; 607/20
(58) Field of Classification Search
USPC ..... 600/484–486, 508–509, 529; 607/18–20, 607/42
See application file for complete search history.

(56) References Cited

U.S. PATENT DOCUMENTS

| 6,415,183 | B1 | 7/2002 | Scheiner et al. |
|---|---|---|---|
| 6,641,542 | B2 | 11/2003 | Cho et al. |
| 6,731,978 | B2 | 5/2004 | Olson et al. |
| 6,731,984 | B2 | 5/2004 | Cho et al. |
| 6,752,765 | B1 | 6/2004 | Jensen et al. |
| 7,025,730 | B2 | 4/2006 | Cho et al. |
| 7,101,339 | B2 | 9/2006 | Daum et al. |
| 7,130,687 | B2 | 10/2006 | Cho et al. |
| 7,206,635 | B2 | 4/2007 | Cho et al. |
| 7,277,757 | B2 | 10/2007 | Casavant et al. |
| 7,421,296 | B1* | 9/2008 | Benser et al. ............. 607/42 |
| 7,488,291 | B2 | 2/2009 | Cho et al. |
| 7,524,292 | B2 | 4/2009 | Cho et al. |
| 7,623,917 | B2 | 11/2009 | Cho et al. |
| 7,874,992 | B2 | 1/2011 | Cho et al. |
| 2005/0065563 | A1 | 3/2005 | Scheiner |
| 2005/0085734 | A1 | 4/2005 | Tehrani |
| 2007/0118183 | A1* | 5/2007 | Gelfand et al. ............. 607/42 |
| 2007/0179385 | A1* | 8/2007 | Cho et al. ............. 600/485 |
| 2008/0188904 | A1 | 8/2008 | Tehrani et al. |
| 2008/0208282 | A1 | 8/2008 | Gelfand et al. |
| 2008/0288010 | A1 | 11/2008 | Tehrani et al. |
| 2008/0288015 | A1 | 11/2008 | Tehrani et al. |
| 2009/0036947 | A1 | 2/2009 | Westlund et al. |
| 2009/0209880 | A1 | 8/2009 | Jensen et al. |
| 2010/0137931 | A1 | 6/2010 | Hopper et al. |
| 2011/0060380 | A1 | 3/2011 | Gelfand et al. |

OTHER PUBLICATIONS

Aivazyan et al., "Autogenic training in the treatment and secondary prevention of essential hypertension: five-year follow-up," *Health Psychol.*, 1988; 7 (Suppl): 201-208.

(Continued)

*Primary Examiner* — Rex R Holmes
(74) *Attorney, Agent, or Firm* — Carol P. Barry

(57) ABSTRACT

Medical devices and methods for providing breathing therapy (e.g., for treating heart failure, hypertension, etc.) may determine at least the inspiration phase of one or more breathing cycles based on the monitored physiological parameters and control delivery of a plurality of breathing therapy sessions (e.g., each of the breathing therapy sessions may be provided during a defined time period). Further, each of the plurality of breathing therapy sessions may include delivering stimulation after the start of the inspiration phase of each of a plurality of breathing cycles to prolong diaphragm contraction during the breathing cycle.

31 Claims, 10 Drawing Sheets

(56) References Cited

OTHER PUBLICATIONS

American Heart Association, "Heart Disease and Stroke Statistics—2010 Update," [Retrieved from the Internet Jul. 25, 2011]. Retrieved from the Internet: <URL: http://myamericanheart.org/idc/groups/ahamah-public/@wcm/@sop/documents/downloadable/ucm_319689.pdf>, 75 pgs.

Bernardi et al., "Effect of breathing rate on oxygen saturation and exercise performance in chronic heart failure," Lancet, May 2, 1998; 351(9112):1308-1311.

Bernardi et al., "Slow breathing increases arterial baroreflex sensitivity in patients with chronic heart failure," Circulation, Jan. 15, 2002; 105:143-145.

Clinical Trial, "Impact of a psychological biofeedback-relaxation intervention on clinical, physical and psychological outcomes in patients with heart failure," ClinicalTrials.gov Identifier: NCT00255931; Sponsor: National Institute of Nursing Research. Project dates Jul. 2004 to May 2010. [Retrieved on Jul. 25, 2011]. Retrieved from the Internet: <URL: http://clinicaltrials.gov/ct2/show/NCT00255931>; 3 pgs.

Clinical Trial, "Short-term hemodynamic effects of controlled slow breathing with biofeedback in patients with heart failure," ClinicalTrials.gov Identifier: NCT00971386; Sponsor: Albert Einstein Healthcare Network. Project dates Feb. 2008 to Oct. 2009. [Retrieved on Jul. 25, 2011]. Retrieved from the Internet: <URL: http://clinicaltrials.gov/ct2/show/NCT00971386>; 4 pgs.

Cowan et al., "Power spectral analysis of heart rate variability after biofeedback training," J Electrocardiol., 1990; 23 Suppl:85-94.

Del Pozo et al., "Biofeedback treatment increases heart rate variability in patients with known coronary artery disease," Am. Heart J., 2004; 147(3):G1-G6.

Durand et al., "Acute and chronic electrical activation of baroreceptor afferents in awake and anesthetized subjects," Braz. J Med. Biol. Res., Jan. 2009; 42:53-60.

Elliot et al., "Graded blood pressure reduction in hypertensive outpatients associated with use of a device to assist with slow breathing," J Clin. Hypertens., Oct. 2004; 6(10):553-561.

Goldsmith et al., "Angiotensin II and sympathetic activity in patients with congestive heart failure," J Am. Coll. Cardiol., Apr. 1993; 15(5):1107-1113.

Goso et al., "Respiratory modulation of muscle sympathetic nerve activity in patients with chronic heart failure," Circulation, Jul. 24, 2001; 104:418-423.

Grossman et al., "Respiratory sinus arrhythmia and parasympathetic cardiac control: some basic issues concerning quantification, application and implications" in Grossman et al. (eds), Cardiorespiratory and Cardiosomatic Psychophysiology, Plenum Press, New York, NY, 1986; 117-138.

Jerath et al., "Augmentation of mind-body therapy and role of deep slow breathing," J Complementary and Integrative Medicine, 2009; 6(1), Article 31; 9 pgs.

Kostis et al., "Superiority of nonpharmacologic therapy compared to propranolol and placebo in men with mild hypertension: a randomized, prospective trial," Am. Heart J., Feb. 1992; 123(2):466-474.

Kranitz et al., "Biofeedback applications in the treatment of cardiovascular diseases," Cardiology Review, May-Jun. 2004;12(3):177-181.

Kukin, "β-blockers in chronic heart failure: considerations for selecting an agent," Mayo Clin. Proc., 2002; 77:1199-1206.

La Rovere et al., "Baroreflex sensitivity and heart-rate variability in prediction of total cardiac mortality after myocardial infarction," Lancet, Feb. 14, 1998; 351(9101):478-484.

Lehrer et al., "Heart rate variability biofeedback increases baroreflex gain and peak expiratory flow," Psychosom. Med., 2003; 65:796-805.

Lehrer et al., "Resonant frequency biofeedback training to increase cardiac variability: rationale and manual for training," Appl. Psychophysiol. Biofeedback, Sep. 2000; 25(3):177-191.

Li et al., "Vagal nerve stimulation markedly improves long-term survival after chronic heart failure in rats," Circulation, Jan. 2004; 109:120-124. Available online Dec. 8, 2003.

Lopshire et al., "Spinal cord stimulation improves ventricular function and reduces ventricular arrhythmias in a canine postinfarction heart failure model," Circulation, Jul. 28, 2009; 120(4): 286-294. Available online Jul. 13, 2009.

Mangin et al., "Altered baroreflex gain during voluntary breathing in chronic heart failure," Eur. J. Heart Fail., Mar. 2001; 3:189-195.

McGrady et al., "Effect of biofeedback-assisted relaxation on blood pressure and cortisol levels in normotensives and hypertensives," J. Behav. Med., Jun. 1987; 10(3):301-310.

Moravec, "Biofeedback therapy in cardiovascular disease: rationale and research overview," Cleve. Clin. J. Med., Mar. 2008; 75(Suppl. 2):S35-S38.

Moser et al., "Voluntary control of vascular tone by using skin-temperature biofeedback-relaxation in patients with advanced heart failure," Altern. Ther. in Health Med., Jan. 1997; 3(1): 51-59.

Navaneethan et al., "Baroreflex stimulation: a novel treatment option for resistant hypertension," J. Am. Soc. Hypertens., 2009; 3(1):69-74.

Nogawa et al., "Assessment of slow-breathing relaxation technique in acute stressful tasks using a multipurpose non-invasive beat-by-beat cardiovascular monitoring system," Proceedings of the 29th Annual International Conference of the IEEE EMBS, 2007:5323-5325; Lyon, France, Aug. 23-26, 2007.

Nolan et al., "Heart rate variability biofeedback as a behavioral neurocardiac intervention to enhance vagal heart rate control," Am. Heart J., Jun. 2005; 149(6):1137e1-1137e7.

Parati et al., "Respiration and Blood Pressure," In: Izzo et al., Hypertension Primer: The Essentials of High Blood Pressure, 3rd Edition, Chapter A40; American Heart Association, 2003. Lippincott Williams & Wilkins, Philadelphia, PA; 6 pgs.

Sanders et al., "Arterial baroreflex control of sympathetic nerve activity during elevation of blood pressure in normal man: dominance of aortic baroreflexes," Circulation, Feb. 1988; 77(2):279-288.

Schein et al., "Treating hypertension with a device that slows and regularises breathing: a randomised, double-blind controlled study," Journal of Human Hypertension, 2001;15:271-278.

Swanson et al., "The effect of biofeedback on function in patients with heart failure," Appl. Psychophysiol. Biofeedback, 2009; 34:71-91. Published online Feb. 10, 2009.

Tanaka et al., "Mechanisms of sustained cutaneous vasodilation induced by spinal cord stimulation," Autonomic Neuroscience: Basic and Clinical, 2004; 114:55-60.

Vaschillo et al., "Heart rate variability biofeedback as a method for assessing baroreflex function: a preliminary study of resonance in the cardiovascular system," Applied Psychophysiology and Biofeedback, Mar. 2002; 27(1):1-27.

Viskoper et al., "Nonpharmacologic treatment of resistant hypertensives by device-guided slow breathing exercises," American Journal of Hypertension, Jun. 2003; 16(6):484-487.

* cited by examiner

MEDICAL DEVICE TO PROVIDE BREATHING THERAPY

The disclosure herein relates to devices and/or methods for treating conditions, such as heart failure, hypertension, etc., using breathing therapy.

Heart failure typically refers to the inability of the heart to keep up with the functional demands made upon it. Congestive heart failure typically refers to an inability of the heart to pump an adequate amount of blood to the body tissues. In other words, congestive heart failure is characterized by inadequate cardiac output.

Because the heart is unable to pump an adequate amount of blood, blood returning to the heart becomes congested in the venous and pulmonary system. A patient with congestive heart failure may be unable to pump enough blood forward to provide an adequate flow of blood to the kidneys, for example, causing the patient to retain excess water and salt. The patient's heart may also be unable to handle the blood returning from the patient's pulmonary system, resulting in a damming of the blood in the lungs and increasing the risk of developing pulmonary edema.

Symptoms experienced by a patient with congestive heart failure may include breathing difficulty caused by pulmonary edema, swelling, particularly of the lower extremities, fatigue, difficulty concentrating, dizziness, and fainting. During periods where a patient with congestive heart failure is experiencing severe symptoms, breathing difficulty may be such that the patient cannot lie down to sleep, and the patient may feel as though they are suffocating.

Patients with congestive heart failure may be treated with pharmacological therapies to increase cardiac output. Some patients with congestive heart failure benefit from an implanted pacemaker that increases cardiac output by increasing the heart rate, or synchronizing the contraction of the ventricles of such patients. When a patient experiences severe symptoms, the patient may be admitted to a hospital or clinic, and receive supplemental pharmacological therapy to alleviate the symptoms. This situation may be very costly because of the hospital stay, nursing costs, patient transportation costs, and so forth.

Generally, chronic heart failure (HF) is accompanied by a sustained elevation in sympathetic nervous system activity (e.g., a sustained elevation of sympathetic tone) which is thought to be an important component in the pathophysiology and progression of the disease. Hypertension or elevated blood pressure is generally indicative of an elevated sympathetic tone. Further, HF patients may also show abnormal breathing patterns with an increased respiratory rate and a lower tidal volume. Faster respiratory rate is associated with higher levels of sympathetic activity and has a negative impact on the functioning of the heart. All these factors contribute to the distressing symptoms of fatigue, dyspnea and exercise intolerance in these patients.

It has been shown that when a slow breathing technique was taught to patients with heart failure (e.g., employing a scripted technique that directed patients to modify their breathing rate), they had a reduction in their sensation of shortness of breath and an improvement in their exercise performance (see, Swanson et al., "The effect of biofeedback on function in patients with heart failure" *Appl Psychophysiol Biofeedback*, 2009; 34(2):71-91). Further, studies have shown that slow breathing, when directed and performed routinely, can lower blood pressure (see Elliot et al., "Graded blood pressure reduction in hypertensive outpatients associated with use of a device to assist with slow breathing," *J Clin Hypertens*, 2004; 6(10):553-9; and Viskoper et al., "Nonpharmacologic Treatment of Resistant Hypertensives By Device-Guided Slow Breathing Exercises," *AJH*, 2003; 16:484-487.

Further, U.S. Pat. App. Pub. No. US2007/0118183 to Gelfand et al., published May 24, 2007, and entitled "System and Method to Modulate Phrenic Nerve to Prevent Sleep Apnea," describes a device for treating breathing disorders such as central sleep apnea using stimulation provided to the phrenic nerve through a transvenous lead system. Unlike other breathing modification devices, such as "Breathing Pacemakers" of Avery Biomedical Devices, Inc. that stimulate the phrenic nerves to cause diaphragm contraction, U.S. Pat. App. Pub. No. US2007/0118183 describes use of stimulation beginning after inspiration to extend the duration of a breath and to hold the diaphragm in a contracted condition (e.g., prolong diaphragm contraction).

SUMMARY

The disclosure herein relates generally to the use of diaphragm contraction prolongation during breathing therapy sessions (e.g., when a patient is not cognitive of respiratory control, such as when they are sleeping) to treat, for example, one or more characteristics of heart failure or hypertension (e.g., which may be determined or identified by an increase in sympathetic tone, such as by an elevated blood pressure). Such breathing therapy may, for example, restore or simulate cardiopulmonary biofeedback to provide biofeedback therapy, e.g., to improve respiratory sinus arrhythmia (RSA), heart rate variability (HRV), etc. Use of breathing therapy sessions that apply diaphragm contraction prolongation, such as when a patient is not cognitive of respiratory control, may not even be noticeable to a patient. The prolongation may effectively extend the respiratory cycle of the patient and, for example, continued or continuous application of the technique during breathing sessions may slow the breathing rate. For example, diaphragm contraction prolongation (DCP) can be activated one or more times (e.g., therapy sessions) during each of one or more days (i.e., during 24 hour periods) and continued for a predetermined duration (e.g., 15-30 minutes) during each of such times (e.g., during each therapy session).

An exemplary medical device (e.g., an implantable medical device) for providing breathing therapy may include monitoring apparatus configured to monitor one or more physiological parameters of a patient (e.g., may include an electrode as part of a lead to monitor one or more physiological parameters of a patient such as termination of an inspiration phase of a breathing cycle); a therapy delivery module configured to deliver electrical stimulation to a patient in which the presence of an elevated sympathetic tone (e.g., temporary or sustained) has been determined (e.g., the elevated sympathetic tone may be determined based at least on an elevated blood pressure); and a control module. The control module may be configured to determine at least the inspiration phase of one or more breathing cycles based on the monitored physiological parameters and control delivery of a plurality of breathing therapy sessions. For example, each of the breathing therapy sessions may be provided during a defined time period, and further wherein each of the plurality of breathing therapy sessions may include delivering stimulation after the start of the inspiration phase of each of a plurality of breathing cycles (e.g., such as prior to termination of the inspiration phase of such breathing cycles) to prolong diaphragm contraction during the breathing cycle.

One or more embodiments of the medical device may include one or more of the following features: the control module may be configured to determine the presence of a sustained elevation of sympathetic tone of a patient based on the monitored one or more physiological parameters of a patient; the therapy delivery module may be configured to deliver at least one of phrenic nerve stimulation, diaphragmatic stimulation, intercostal muscle stimulation, and central respiratory control center stimulation; the control module may be configured to provide one or more breathing therapy sessions during each of a plurality of days; the control module may be configured to determine a current breathing cycle length for the patient and duration of the inspiration phase of the current breathing cycle, provide a target breathing cycle length for the patient, and control delivery of stimulation after the start of the inspiration phase of each of a plurality of breathing cycles and prior to termination of the inspiration phase of such breathing cycles to provide an increasing diaphragm contraction prolongation over the plurality of breathing cycles until the target breathing cycle length of the patient is attained (e.g., delivery of stimulation may be controlled such that the duration of the stimulation delivered over the plurality of breathing cycles follows an increasing linear function); the control module may be configured to control delivery of stimulation such that, during each of the plurality of breathing therapy sessions, stimulation is continued after the target breathing cycle length of the patient is attained to maintain the target breathing cycle length of the patient until the end of the predefined time period for the breathing therapy session; the therapy module may be configured for delivering cardiac stimulation with the control module being configured to control delivery of cardiac pacing to the patient based on predefined ratios of breathing rate to heart rate; the control module may be configured to control delivery of cardiac pacing to the patient based on a predefined ratio of inspiration pacing rate to expiration pacing rate; the control module may be configured to determine when a patient is sleeping and to provide the plurality of breathing therapy sessions when the patient is sleeping; the control module may be configured to determine the presence of an elevated sympathetic tone by at least one of determining the presence of at least one of an elevated blood pressure, an elevated heart rate, a decreased heart rate variability, decreased muscle sympathetic nerve activity, a decreased galvanic skin response, and an increased respiratory rate; the control module may be configured to determine a change in the elevated sympathetic tone and may be configured to adjust one or more parameters of one or more breathing therapy sessions based thereon; the control module may be configured to determine a change in at least blood pressure of the patient to determine a change in the elevated sympathetic tone and may be configured to adjust one or more parameters of one or more breathing therapy sessions based thereon; and the control module may be configured to define a schedule to provide the plurality of breathing therapy sessions (e.g., each of the breathing therapy sessions may be provided during a defined tie period such that a patient attains a target breathing cycle length during the breathing therapy session).

One exemplary method described herein for providing breathing therapy may include monitoring one or more physiological parameters of a patient to determine the presence of an elevated sympathetic tone, monitoring respiration of a patient to determine at least the inspiration phase of one or more breathing cycles, and providing a plurality of breathing therapy sessions upon determination of the presence of an elevated sympathetic tone (e.g., temporary or sustained). Each of the breathing therapy sessions may be provided during a defined time period, and further, each of the plurality of breathing therapy sessions may include delivering stimulation after the start of the inspiration phase of a plurality of breathing cycles (e.g., prior to termination of the inspiration phase of such breathing cycles) to prolong diaphragm contraction during the breathing cycle.

One or more embodiments of the exemplary method may include one or more of the following steps, processes, or features: delivering at least one of phrenic nerve stimulation, diaphragmatic stimulation, intercostal muscle stimulation, and central respiratory control center stimulation to control the breathing cycle of the patient (e.g., stimulating after the start of the inspiration phase of each of a plurality of breathing cycles to prolong diaphragm contraction during the breathing cycle); providing one or more breathing therapy sessions during each of a plurality of days; providing each of the plurality of breathing therapy sessions by determining a current breathing cycle length for the patient and duration of the inspiration phase of the current breathing cycle, setting a target breathing cycle length for the patient, delivering stimulation after the start of the inspiration phase of each of a plurality of breathing cycles and prior to termination of the inspiration phase of such breathing cycles to provide an increasing diaphragm contraction prolongation over the plurality of breathing cycles until the target breathing cycle length of the patient is attained (e.g., the duration and or amplitude of the stimulation delivered over the plurality of breathing cycles may follow an increasing linear function); continuing stimulation after the target breathing cycle length of the patient is attained to maintain the target breathing cycle length of the patient until the end of the predefined time period for the breathing therapy session; delivering cardiac pacing (e.g., during the breathing therapy sessions) to the patient based on a predefined ratio of breathing rate to heart rate; delivering cardiac pacing (e.g., during the breathing therapy sessions) to the patient based on a predefined ratio of inspiration pacing rate to expiration pacing rate; providing the plurality of breathing therapy sessions when the patient is not cognitive of respiratory control; determining when the patient is sleeping and providing the plurality of breathing therapy sessions when the patient is sleeping; determining the presence of an elevated sympathetic tone by determining the presence of at least one of an elevated blood pressure, an elevated heart rate, a decreased heart rate variability, decreased muscle sympathetic nerve activity, a decreased galvanic skin response, and an increased respiratory rate; monitoring the one or more physiological parameters of a patient to determine a change in the elevated sympathetic tone (e.g., elevated blood pressure) and adjusting one or more characteristics of one or more breathing therapy sessions based thereon; and defining a schedule to provide the plurality of breathing therapy sessions (e.g., each of the breathing therapy sessions may be provided during a defined tie period such that a patient attains a target breathing cycle length during the breathing therapy session).

Still further, in one or more embodiments of the medical device and/or methods, the device may be configured to operate in combination with one or more additional therapy apparatus configured to provide delivery of one or more additional therapies during each of the plurality of breathing therapy sessions. For example, the one or more additional therapies may include at least one of carotid sinus stimulation, aortic baroreceptor stimulation, baroreflex activation therapy, vagus nerve stimulation, cardiac synchronization therapy, cardiac pacing, spinal cord stimulation, renal nerve block, and drug therapy.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
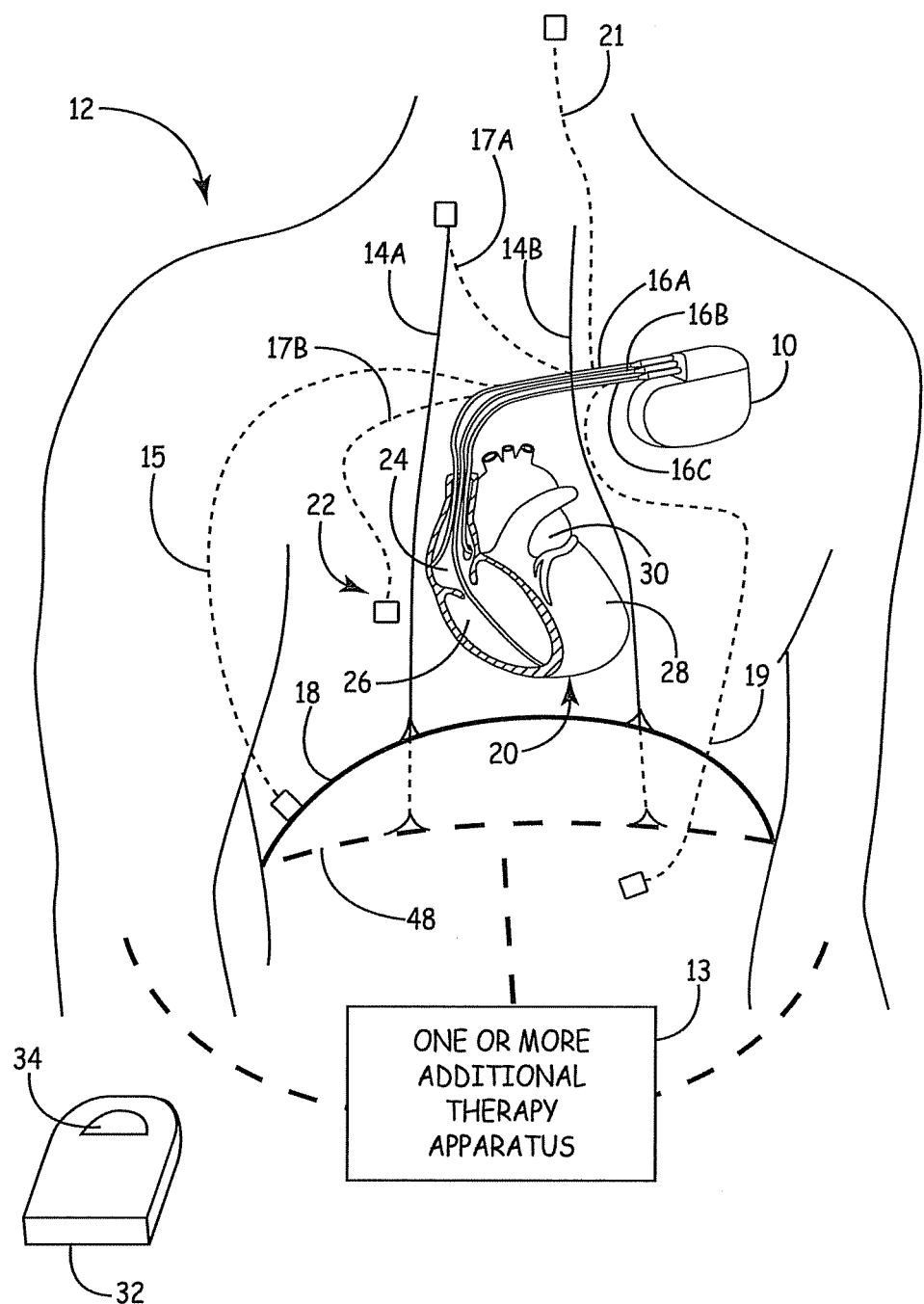
FIG. 1 is a schematic diagram illustrating exemplary embodiments of an implantable medical device (IMD) to provide breathing therapy.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-10. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Elevated (e.g., increased) sympathetic tone may be associated with the progression of heart failure. For example, temporary or sustained elevated sympathetic tone (e.g., which may be indicated by elevated blood pressure or hypertension) may contribute to the progression of heart failure. Use of breathing therapy (e.g., automatically controlled breathing therapy, for example, such as may be delivered when a person is not cognitive of respiratory control) as described herein may reduce the progression of heart failure or improve hypertension, e.g., may improve respiratory sinus arrhythmia (RSA), may increase heart rate variability (HRV), may increase arterial baroreflex sensitivity, may decrease blood pressure, may decrease heart rate, may decrease muscle sympathetic nerve activity (MSNA), may decrease galvanic skin response (e.g., may decrease skin conductance properties; also referred to a electrodemial response (EDR)), may decrease respiratory rate, etc.

In one embodiment of one or more processes described herein, one exemplary advantage of using the diaphragm contraction prolongation technique over other phrenic nerve stimulation techniques may be that it minimizes certain undesirable effects on the subject. For example, such a technique may be much more tolerable to a patient (e.g., may not even be noticeable) as opposed to, for example, use of continuous stimulation of the phrenic nerve. Yet, diaphragm contraction prolongation extends the respiratory cycle and application of this technique over a plurality of therapy sessions may slow the breathing rate of a patient.

Breathing therapy as described herein may be implemented by one or more various devices (e.g., a medical device that includes multiple devices or components operable together or separately, an implantable medical device, etc.) and/or systems. Such devices and systems may include one or more leads, electronic circuits, power sources, sensors, electrodes, stimulation devices, monitoring devices, etc. One example of a medical device that may be used in carrying out breathing therapy as described herein is depicted in FIG. 1 as a schematic diagram of an implantable medical device (IMD).

The IMD 10, or another monitoring apparatus operable separately or in combination with the IMD 10, may be configured to monitor one or more physiological parameters of a patient (e.g., electrical activity of a patient, chemical activity of a patient, hemodynamic activity of a patient, and respiratory activity of a patient). The monitored physiological parameters, in turn, may be used to determine whether the patient has an elevated sympathetic tone (e.g., temporary or sustained), which may be indicated by an elevated blood pressure (e.g., arterial blood pressure) or hypertension. For example, in one embodiment, the IMD 10 may determine that an elevated sympathetic tone state exists (e.g., such that breathing therapy may be beneficial). For example, such an elevated sympathetic tone may be determined based on hemodynamic measurements of blood pressure.

As used herein, a temporary elevated sympathetic tone refers to a sympathetic tone that is determined to be elevated based on measurements (e.g., a single measurement or multiple measurements made over a period of time) but which returns to normal at a later time (e.g., such an elevated condition may reoccur or not reoccur). As used herein, a sustained elevated sympathetic tone (e.g., a chronic condition) refers to a sympathetic tone that is elevated over a long duration or there is a frequent recurrence of such elevated tone over a long duration of time (e.g., determined based on measurements made over a relatively long period of time). For example, further, whether a parameter herein is "elevated" may be based on a comparison to what is "normal" for an individual or "normal" for an average person in a similar population.

As shown in FIG. 1, implantable medical device ("IMD") 10 is implanted within a patient 12. IMD 10 may be used to provide breathing therapy as described herein (e.g., using diaphragm contraction prolongation) by, for example, stimulation of one or both of right phrenic nerve 14A and left phrenic nerve 14B (collectively "phrenic nerves 14") via one or more of leads 16A, 16B, and 16C (collectively "leads 16"), as shown in FIG. 1. Stimulation of phrenic nerves 14 by IMD 10 as described further herein after the start of the inspiration phase (e.g., prior to termination of the inspiration phase) causes prolongation of contraction of diaphragm 18. Repeated stimulation of phrenic nerves 14 by IMD 10 during one or more breathing therapy sessions, may, as will be described herein, decrease a patient's breathing rate, e.g., over the long term. For example, IMD 10 may control the delivery of a plurality of breathing therapy sessions. Each of the breathing therapy sessions, for example, may be provided during a defined time period. Further, for example, each of the plurality of breathing therapy sessions may include delivering stimulation after the start of the inspiration phase of each of a plurality of breathing cycles (e.g., prior to termination of the inspiration phase of such breathing cycles, at the start of expiration, after the start of expiration, etc.) to prolong diaphragm contraction during the breathing cycle (e.g., increase the breathing cycle length).

IMD 10 may include any number of leads 16. Leads 16 may, as shown in FIG. 1, extend into heart 20. For example, leads 16 may be intravascular leads, i.e., enter heart 20 via one or more veins (not shown) of patient 12. The configuration of leads 16 shown in FIG. 1 is merely exemplary and any configuration of leads that provides for suitable stimulation as described herein may be used. For example, such leads may be positioned with electrodes proximate the phrenic nerves and not within the heart (e.g., in configurations that do not also use cardiac pacing).

Each of leads 16 may include one or more electrodes (not shown) for delivering stimulation to phrenic nerves 14. Such electrodes may deliver stimulation to phrenic nerves 14 through the tissues of heart 20 or the veins. Leads 16 may also include electrodes by which IMD 10 may sense electrical activity within heart 20, e.g., sense electrical signals attendant to the depolarization and re-polarization of heart 20, deliver pacing pulses to heart 20, deliver defibrillation shocks to heart 20, and/or monitor pressure or oxygen saturation within heart 20 or otherwise within the cardiovascular system of patient 12. The electrodes for delivering stimulation to phrenic nerves 14, sensing electrical activity, and delivering pulses may be unipolar or bipolar electrodes, as is well known in the art.

IMD 10 is not limited to use with intravascular leads 16, or intravascular or intracardiac electrodes. IMD 10 may deliver stimulation to phrenic nerves 14, sense electrical activity, deliver pacing pulses, deliver defibrillation shocks, and monitor pressure or oxygen saturation from any appropriate site within or outside of patient 12. For example, IMD 10 may stimulate phrenic nerves 14 via leads 16 that extend to any point along phrenic nerves 14, such as a lead that may extend to a point of a phrenic nerve near the neck of patient 12, a lead that may extend to a phrenic nerve proximate the heart, a lead that includes coil electrodes that coil around phrenic nerves 14 (all represented generally by dashed lines/electrode 17A-17B), as would be known to one skilled in the art.

Although the description herein is provided primarily with respect to the use of phrenic nerve stimulation to provide breathing therapy, other stimulation may be used to provide such breathing therapy. For example, as shown generally by dashed lead(s)/electrode(s) 15, intercostal muscle stimulation may be used. For example, lead(s) may carry electrode(s) proximate points associated with the intercostal muscles, which play a role in respiration, for stimulation thereof to carry out diaphragm contraction prolongation. Further, for example, as shown generally by dashed lead(s)/electrode(s) 19, diaphragmatic stimulation may be used. For example, lead(s) may carry electrode(s) proximate points associated with the diaphragm for stimulation thereof to carry out diaphragm contraction prolongation. For example, stimulation may be delivered to the lower thoracic/upper lumbar region of the spinal cord to stimulate nerves associated with the intercostal muscles. Further, for example, electrodes may be inserted directly into the diaphragm muscle, generally near the motor point (e.g., where the phrenic nerve enters the diaphragm), electrodes may be placed in arterial or veins close to the phrenic nerve (e.g., placed in the pericardiophrenic vein, either unilaterally (such as the left side only) or bilaterally), electrodes may be placed along side the phrenic nerve, cuff electrodes may be placed around the phrenic nerve, etc.

Still further, for example, as shown generally by dashed lead(s)/electrode(s) 21, central respiratory control center stimulation may be used. For example, lead(s) may carry electrode(s) proximate points in the medullary centers of the brain which play a role in respiration. Stimulation thereof may be carried out to provide diaphragm contraction prolongation.

In one or more embodiments, a single type of stimulation or multiple types of stimulation may be used to provide diaphragm contraction prolongation during breathing cycles. For example, phrenic nerve stimulation may be use alone, or, in at least another alternate embodiment, an IMD may first stimulate phrenic nerves and then shortly thereafter stimulate the diaphragm or the intercostal muscles to provide diaphragm contraction prolongation.

Still further, for example, as shown in FIG. 1, one or more additional therapy apparatus 13 may be included to provide additional therapy in combination with diaphragm contraction prolongation in combination with (e.g., before, during, or after) one or more breathing sessions. For example, such additional therapy apparatus 13 may include apparatus for providing at least one of carotid sinus stimulation, aortic baroreceptor stimulation, baroreflex activation therapy, vagus nerve stimulation, spinal cord stimulation, renal nerve block, and drug therapy.

For example, baroreflex activation therapy or baroreceptor stimulation, such as carotid sinus stimulation may be provided using electrodes placed in or around the carotid artery, e.g., at the carotid sinus location. Further, for example, aortic baroreceptor stimulation may be provided using electrodes on, in or near the aortic arch. For example, one or more embodiments of such therapies and apparatus for delivering such therapies are described in the following articles: Navaneethan, et al., Baroreflex stimulation: A novel treatment option for resistant hypertension, *Journal of the American Society of Hypertension,* 3(1) 69-74 (2009); Durand, et al., Acute and chronic electrical activation of baroreceptor afferents in awake and anesthetized subjects, *Brazilian Journal of Medical and Biological Research,* 42: 53-60 (2009); and Sanders, et al., Arterial baroreflex control of sympathetic nerve activity during elevation of blood pressure in normal man: dominance of aortic baroreflexes, *Pathophysiology and Natural History-Hypertension*, Vol. 77, No. 2, (February 1998).

For example, spinal cord stimulation may be provided using electrodes placed in or proximate to the spinal cord at a level to stimulate cardiac nerves. For example, one or more embodiments of such therapies and apparatus for delivering such therapies are described in the articles, Tanaka et al., Mechanisms of sustained cutaneous vasodilation induced by spinal cord stimulation, *Autonomic Neuroscience: Basic and Clinical*, 114, pp. 55-60 (2004); and Lopshire, et al., Spinal Cord Stimulation Improves Ventricular Function and Reduces Ventricular Arrhythmias in a Canine Postinfarction Heart Failure Model, *Circulation*, 120:286-294 (July 2009).

For example, renal nerve block may be provided using renal nerve ablation. For example, the therapy may involve the use of ablation apparatus to ablate one or more portions of the renal nerve (e.g., to assist in controlling hypertension). In addition, drug therapy may be provided using, for example, oral medication, drug pumps, or any other apparatus for treating a condition (e.g., such as hypertension) with one or more drugs.

Further, for example, vagus nerve stimulation may be carried out using leads 16 having electrodes positioned proximate the vagus nerve. For example, use of such therapy in the context of heart failure is described in Li, et al., Vagal Nerve Stimulation Markedly Improves Long-Term Survival After Chronic Heart Failure in Rats, *Circulation*, 109:120-124 (January 2004).

Still further, as described herein, the IMD 10 may be used to provide cardiac synchronization therapy or cardiac pacing in combination with diaphragm contraction prolongation during breathing cycles. For example, the pacing may be controlled based on one or more respiratory characteristics (e.g., controlled to provide a certain number of heart beats per breath cycle, controlled to provide a certain number of heart beats in the inspiration or expiration phase of the breath cycle, controlled to provide a certain ratio of heart beats in the inspiration phase to the expiratory phase, etc.). One or more embodiments of using pacing with diaphragm contraction prolongation during breathing cycles are described herein with reference to FIGS. 8-9.

In other words, for example, one or more additional therapy apparatus 13 may be included to provide one or more of the additional therapies in combination with diaphragm contraction prolongation. Various types of apparatus may be used to provide such additional therapies, and the present disclosure is not limited to only those listed or provided in the references cited herein.

Further, with reference to FIG. 1, and the use of phrenic nerve stimulation, it will be recognized that either phrenic nerve 14A or phrenic nerve 14B, or both, may be stimulated to provide for diaphragm contraction prolongation. For example, when IMD 10 stimulates right phrenic nerve 14A, a right half of diaphragm 18 contracts. Similarly, when IMD 10 stimulates left phrenic nerve 14B, a left half of diaphragm 18 contracts. Depending on the strength of contraction of one of the right and left halves of diaphragm 18, the other half of diaphragm 18 may be stimulated to contract via mechanical activation. Diaphragm 18 and phrenic nerves 14 are shown in FIG. 1 in their respective positions after diaphragm 18 has contracted as segmented lines. As shown in FIG. 1, when diaphragm 18 contracts, it descends, expanding the volume of thoracic cavity 22.

When diaphragm 18 is in the resting position, the pressure within thoracic cavity 22 is at an equilibrium pressure. When IMD 10 stimulates one or both phrenic nerves 14, causing diaphragm 18 to contract and thoracic cavity 22 to expand, the pressure within thoracic cavity 22 decreases relative to the pressure of the atmosphere outside of patient 12, causing air to enter the lungs (not shown) of patient 12. As air fills the lungs, the pressure within thoracic cavity 22 begins to return to the equilibrium pressure. When diaphragm 18 recoils, the pressure within thoracic cavity 22 increases beyond the equilibrium pressure, forcing air out of the lungs, until the equilibrium pressure is again reached.

Figure 2:
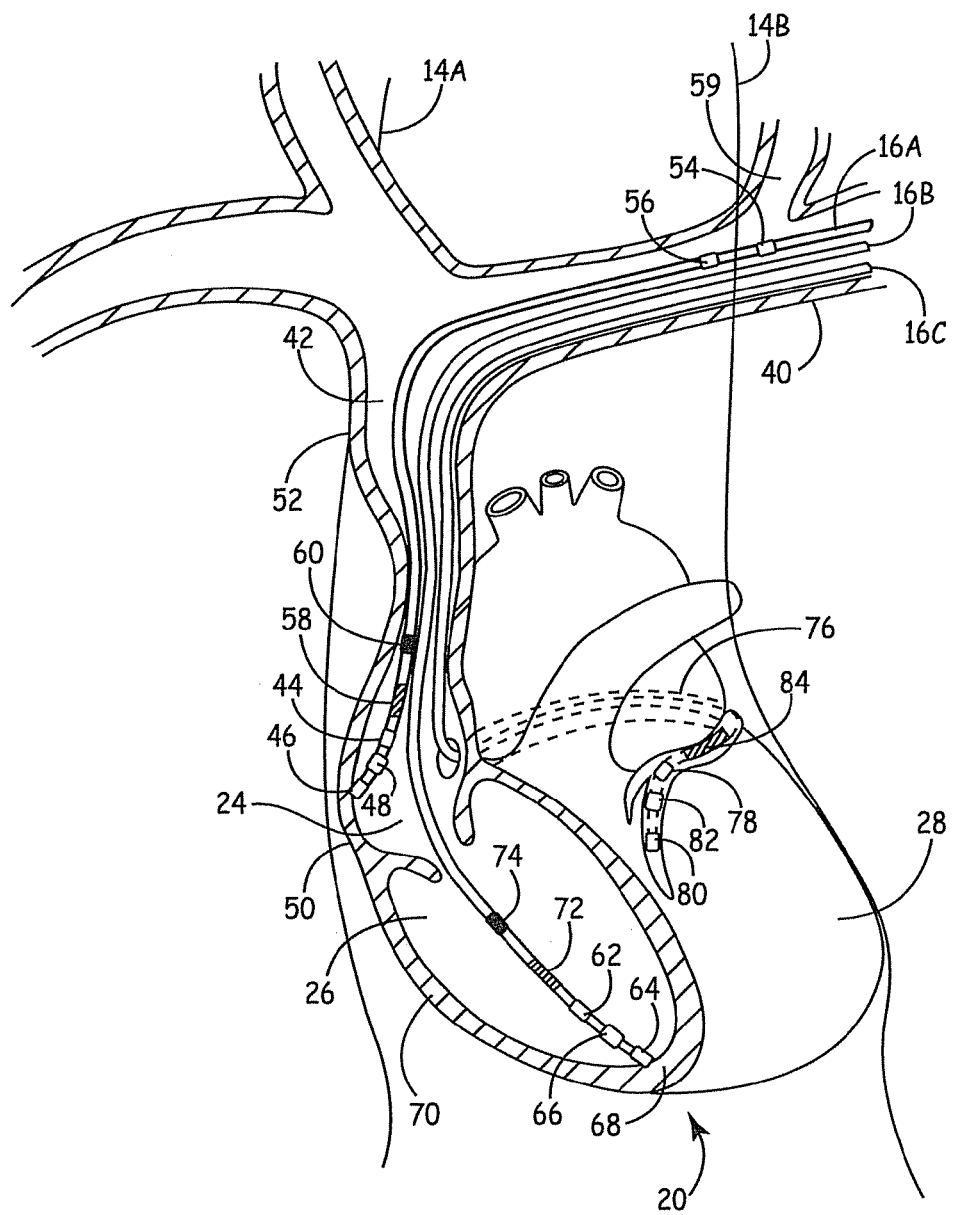
FIG. 2 is a schematic diagram illustrating one embodiment of exemplary implanted leads of an implantable medical device (IMD) operably coupled to a patient's heart.

FIG. 2 is a schematic view further illustrating exemplary leads 16 of IMD 10. Leads 16 may, for example, as shown in FIG. 2, extend from IMD 10 and enter a left subclavian vein 40 of patient 12. As shown in FIG. 2, leads 16 may extend through left subclavian vein 40 and superior vena cava 42, and enter heart 20.

As shown in FIG. 2, lead 16A may extend into right atrium 24. Lead 16A may include an elongated insulative lead body carrying a number of concentric coiled conductors separated from one another by tubular insulative sheaths. Located adjacent distal end of lead 16A are bipolar electrodes 44 and 46. Electrode 44 may take the form of a ring electrode, and electrode 46 may take the form of an extendable helix electrode mounted retractably within an insulative electrode head 48. Each of the electrodes 44 and 46 may be coupled to one of the coiled conductors within the lead body. IMD 10 may stimulate right phrenic nerve 14A via electrodes 44 and 46. IMD 10 may also use electrodes 44 and 46 for atrial pacing and for sensing atrial depolarizations. In one or more embodiments, IMD 10 may include a separate lead 16 with separate electrodes, or separate electrodes on lead 16A for atrial pacing and sensing.

Electrodes 44 and 46 may, as shown in FIG. 2, be located proximate to a lateral wall 50 of right atrium 24. IMD 10 may more easily stimulate right phrenic nerve 14A when electrodes 44 and 46 are proximate to lateral wall 50. The distal end of lead 16A and electrodes 44 and 46 may, in some embodiments, be located proximate to a lateral wall 52 of superior vena cava 42.

In some embodiments, lead 16A may also, as shown in FIG. 2, include bipolar electrodes 54 and 56 located near the junction of left subclavian vein 40 and a left innominate vein 59. IMD 10 may stimulate left phrenic nerve 14B via electrodes 54 and 56. In other embodiments, IMD 10 may stimulate both phrenic nerves 14 with a single stimulus via a first unipolar electrode (not shown) located at the distal end of lead 16A, and a second unipolar electrode (not shown) located near the junction of left subclavian vein 40 and left innominate vein 59. In still other embodiments, electrodes 54 and 56 may be located on lead 16B, or on a lead 16 other than leads 16A-C.

Lead 16A may also, as shown in FIG. 2, include an elongated coil electrode 58 and a pressure sensor 60. Defibrillation electrode 58 and pressure sensor 60 may, as shown in FIG. 2, be located within right atrium 24, or may be located anywhere along lead 16A. IMD 10 may deliver defibrillation therapy to heart 20 via defibrillation electrode 58, and may monitor pressure within right atrium 24 and/or superior vena cava 42 via pressure sensor 60. Defibrillation electrode 58 and pressure sensor 60 may also be located on one or more leads other than lead 16A.

Pressure sensor 60 may sense the absolute pressure of blood within right atrium 24 and/or superior vena cava 42, and may be capacitive or piezoresistive pressure sensor. IMD 10 may, for example, monitor the central venous pressure of heart 20 via pressure sensor 60.

As shown in FIG. 2, lead 16B may extend into right ventricle 26. Like lead 16A, lead 16B may include an elongated insulative lead body carrying a number of concentric coiled conductors separated from one another by tubular insulative sheaths. Located adjacent distal end of lead 16B are bipolar electrodes 62 and 64. Electrode 62 may take the form of a ring electrode, and electrode 64 may take the form of an extendable helix electrode mounted retractably within an insulative electrode head 66. Each of the electrodes 62 and 64 is coupled to one of the coiled conductors within the lead body. IMD 10 may stimulate right phrenic nerve 14A via electrodes 62 and 64. IMD 10 may also use electrodes 62 and 64 for ventricular pacing and for sensing ventricular depolarization. In some embodiments, IMD 10 may include a separate lead 16 with separate electrodes, or separate electrodes on lead 16B for ventricular pacing and sensing.

Electrodes 62 and 64 may, as shown in FIG. 2, be located proximate to an apex 68 of right ventricle 26. IMD 10 may more easily stimulate right phrenic nerve 14A when electrodes 44 and 46 are proximate to apex 68. The distal end of lead 16B and electrodes 62 and 64 may, in some embodiments, be located proximate to a lateral wall 70 of right ventricle 26.

Like lead 16A, lead 16B may include an elongated coil electrode 72 and a pressure sensor 74 located within right ventricle 26. IMD 10 may deliver defibrillation therapy to heart 20 via defibrillation electrode 72, and may monitor pressure within right ventricle 26 via pressure sensor 74. IMD 10 may, for example, estimate a pulmonary artery diastolic pressure via pressure sensor 74. Defibrillation electrode 72 and pressure sensor 74 may be located on one or more leads other than lead 16B.

Lead 16C may extend into a coronary sinus 76 of heart 20 until a distal end of lead 16 is proximate to left ventricle 28. Like leads 16A-B, lead 16C may include an elongated insulative lead body carrying a number of concentric coiled conductors separated from one another by tubular insulative sheaths. Located adjacent distal end of lead 16C are bipolar electrodes 78 and 80 indicated by a broken outline. Electrode 78 may take the form of a ring electrode, and electrode 80 may take the form of an extendable helix electrode mounted retractably within an insulative electrode head 82. Each of the electrodes 78 and 80 is coupled to one of the coiled conductors within the lead body. IMD 10 may stimulate left phrenic nerve 14B via electrodes 78 and 80. IMD 10 may also use electrodes 78 and 80 for ventricular pacing and for sensing ventricular depolarization. Lead 16C may include an elongated coil electrode 84 indicated by a broken outline for delivery of defibrillation therapy to heart 20.

In other words, the IMD 10 may monitor pressure or one or more other physiological parameters of a patient that may indicate an elevated sympathetic tone. However, in one or more embodiments, a different monitoring apparatus may be used (not shown) that monitors one or more physiological parameters of a patient (e.g., that may indicate an elevated sympathetic tone, such as with measurements of arterial blood pressure). For example, the monitor or the IMD may include a pressure monitor, oxygen saturation monitor, etc. A pressure monitor may, for example, monitor the pressure within right ventricle 26 to estimate the pulmonary artery diastolic pressure based on the rate of change of the right ventricular pressure over time. Increased pulmonary artery diastolic pressure may indicate an elevated sympathetic tone (e.g., inadequate cardiac output). A pressure monitor or IMD may also monitor arterial pulse pressure, central venous pressure, right ventricular end diastolic pressure, left ventricular end diastolic pressure, pulmonary capillary wedge pressure, or the like. An oxygen saturation monitor or an IMD may monitor the oxygen saturation of hemoglobin within the arterial and/or venous blood of patient 10. Decreased arterial or venous oxygen saturation, or an increased difference between the arterial and venous oxygen saturations may indicate an elevated sympathetic tone (e.g., inadequate cardiac output). In other words, one or more of such physiological parameters may be measured to determine an elevated sympathetic tone.

Further, IMD 10 may stimulate one or both of phrenic nerves 14 via any one of or combination of the bipolar and unipolar electrodes and electrode locations described herein. Moreover, IMD 10 need not deliver pacing pulses to any chamber 24-28 of heart 20, need not deliver defibrillation therapy to heart 20, and need not monitor pressure within heart 20. The electrodes, sensors, and electrode and sensor locations are merely provided as examples of electrodes, sensors, and electrode and sensor locations that may be used in various embodiments of IMD 10.

Figure 3:
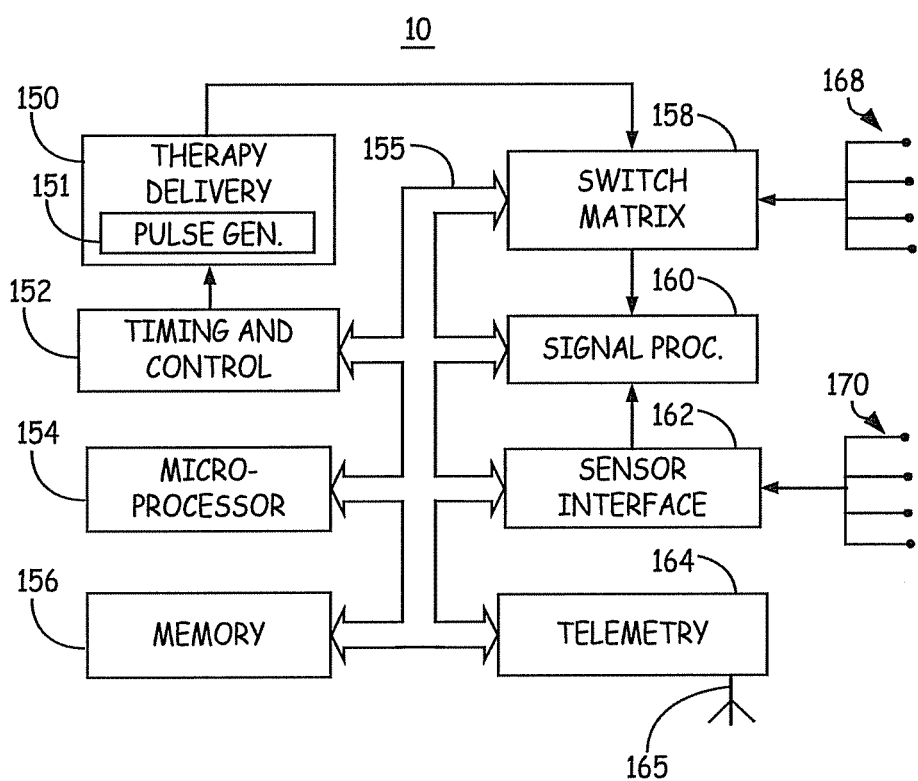
FIG. 3 is a block diagram of an exemplary IMD such as shown in FIG. 1.

FIG. 3 is a general exemplary functional block diagram of an IMD 10, such as shown generally in FIG. 1. IMD 10 generally includes timing and control circuitry 152 and an operating system that may employ microprocessor 154 or a digital state machine for timing sensing and therapy delivery functions and controlling other device functions in accordance with a programmed operating mode. Microprocessor 154 and associated memory 156 are coupled to the various components of IMD 110 via a data/address bus 155. IMD 110 includes therapy delivery module 150 for delivering a breathing therapy, or any other therapy described herein, such as electrical stimulation or drug therapy, under the control of timing and control circuitry 152. Therapy delivery module 150 may include pulse-generating circuitry 151 for generating electrical stimulation pulses (e.g., electrical stimulation pulses) under the control of timing and control circuitry 152. As will be described herein, pulse-generating circuitry 151 may generate stimulation pulses for stimulating the phrenic nerve, intercostal muscles, the diaphragm, medullary centers, etc. for use in providing breathing therapy. Further, for example, as will be described herein, pulse-generating circuitry 151 may generate stimulation pulses for providing pacing of the heart.

For delivering electrical stimulation pulses, pulse-generating circuitry 151 may be coupled to two or more electrodes 168 (e.g., such as implemented by the electrodes of leads 16) via a switch matrix 158. Switch matrix 158 may be used for selecting which electrode and corresponding polarities are used for delivering electrical stimulation pulses. Electrodes 168 may include lead-based electrodes, leadless electrodes incorporated on IMD 10, and/or the IMD housing configured for use as a can or case electrode.

Therapy delivery module 150 may further include high voltage circuitry for generating high voltage cardioversion/defibrillation shocks. Aspects of the present disclosure may be embodied in an implantable cardioverter defibrillator including high voltage circuitry as generally disclosed in U.S. Pat. No. 6,731,978 to Olson et al., incorporated herein by reference in its entirety.

Further, in one or more embodiments, electrodes 168 may also be used for sensing electrical signals within the body, such as cardiac signals or impedance signals, such as for use in monitoring respiration. Electrical signals are sensed using any of electrodes 168 for use in determining the heart rhythm and/or for determining when therapy may be needed, and in controlling the timing of stimulation pulses. In other words, the IMD 10 may include monitoring apparatus, which includes electrodes 168 amongst other things, for determining an elevated sympathetic tone, for monitoring parameters to adjust breathing therapy, for verifying the effectiveness of the breathing therapy, etc.

Electrodes used for sensing and electrodes used for stimulation (e.g., such as implemented by the electrodes of leads 16) may be selected via switch matrix 158. When used for sensing, electrodes 168 may be coupled to signal processing circuitry 160 via switch matrix 158. Processing circuitry 160 may include sense amplifiers and other signal conditioning circuitry, and one or more analog to digital converters. In other words, the IMD 10 may include a sensing module, e.g., includes switch matrix 158, signal processing circuitry 160, etc. Electrically sensed signals may then be used by microprocessor 154 for detecting physiological parameters or events, such as detecting an elevated sympathetic tone, elevated blood pressure, etc.

The monitoring apparatus of the IMD 10 may further include sensors 170 such as pressure sensors, accelerometers, flow sensors, blood chemistry sensors, activity sensors, and/or other physiological sensors known for use with IMDs. Sensors 170 are coupled to IMD 10 via a sensor interface 162 which provides sensor signals to signal processing circuitry 160. Sensor signals may be used by microprocessor 154 for detecting physiological events or conditions (e.g., an elevated sympathetic tone, a sleeping state of a patient, etc.). For example, IMD 10 may monitor heart wall motion, blood pressure, blood chemistry, respiration, and/or patient activity. Monitored signals may be used for sensing the need for delivering, adjusting, terminating, and/or initiating breathing therapy under control of the operating system. In other words, the IMD 10 may include a control module, which may include the microprocessor 154 and memory 156 and may be configured using an operating system.

The operating system includes associated memory 156 for storing a variety of programmed-in operating modes and parameter values that are used by microprocessor 154. The memory 156 may also be used for storing data compiled from sensed signals and/or relating to device operating history (e.g., for use in delivering, adjusting, controlling, initiating, and/or terminating therapy) and/or for communicating such data outside of the patient (e.g., using telemetry communication out of recorded history on receipt of a retrieval or interrogation instruction).

IMD 10 may further include telemetry circuitry 164 and antenna 165. Programming commands or data are transmitted during uplink or downlink telemetry between IMD telemetry circuitry 164 and external telemetry circuitry included in a programmer or home monitoring unit.

For example, in one or more embodiments, such as shown in FIG. 1, IMD 10 may receive a signal from patient 12 indicating a need for breathing therapy (e.g., patient feels short of breath, an increased respiratory rate, etc.) via a patient activator or programmer 32. For example, when patient 12 experiences symptoms that may be treatable using breathing therapy (e.g., such as difficulty breathing), patient 12 may place activator 32 over IMD 10, e.g., by placing activator 32 on the chest of patient 12, and press button 34 to request breathing therapy (e.g., stimulation of phrenic nerves 14 by IMD 10, such as during the next period of time when the patient is sleeping).

It will be recognized that the diagrams of FIGS. 1-3 should be taken as exemplary of the type of device in which various embodiments described herein may be embodied, and not as limiting to such devices. The processes described herein may be practiced in a wide variety of device implementations, including pacemakers (see, for example, FIG. 9), pacemaker-cardioverter-defibrillators, etc. Alternatively, or in combination, such processes may be carried out using implantable nerve stimulators or muscle stimulators, and further, for example, with use of monitoring devices (e.g., cardiac monitoring devices) that do not provide any stimulation (e.g., a monitoring device may be used with a separate stimulation device; such devices provided with a form of communication therebetween).

Figure 4:
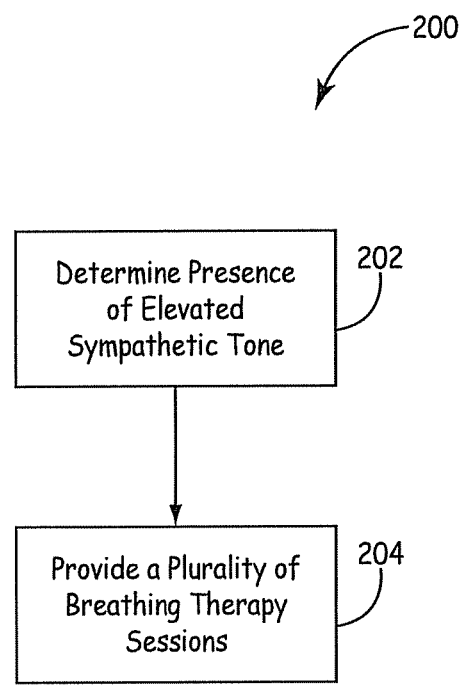
FIG. 4 is a flow chart depicting an exemplary general method of providing breathing therapy, e.g., using diaphragm contraction prolongation.

A generalized method 200, for treating the symptoms of or treating heart failure and/or hypertension, e.g., using diaphragm contraction prolongation, is diagrammatically depicted in the flow chart of FIG. 4. Method 200 (as well as one or more other methods illustrated herein) are intended to illustrate the general functional operation of the devices and/or systems, and should not be construed as reflective of a specific form of software or hardware necessary to practice all of the methods described herein. It is believed that the particular form of software will be determined primarily by the particular system architecture employed in the device (e.g., IMD 10) and by the particular detection and therapy delivery methodologies employed by the device and/or system. Providing software and/or hardware to accomplish the described methods in the context of any modern IMD, or devices usable therewith, given the disclosure herein, is within the abilities of one of skill in the art.

Further, methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The hardware used to accomplish the described methods, may include any one or more of a microprocessor, a digital signal processor (DSP), a controller, an application specific integrated circuit (ASIC), a field programmable gate array (FPGA), or equivalent discrete or integrated logic circuitry. In one or more exemplary embodiments, the processor may include multiple components, such as any combination of one or more microprocessors, one or more controllers, one or more DSPs, one or more ASICs, or one or more FPGAs, as well as other discrete or integrated logic circuitry. The functions and processes described herein may be embodied as software, firmware, hardware, or any combination thereof.

The term "module," "processor," or other like terminology, may generally refer to any of the foregoing circuitry, alone or in combination with other logic circuitry, or any other equivalent circuitry. Such hardware, software, and/or firmware may be implemented within the same device or within separate devices to support the various operations and functions described in this disclosure. In addition, any of the described units, modules, or components may be implemented together or separately as discrete but interoperable devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The method 200 of FIG. 4 includes a determination of the presence of elevated sympathetic tone (block 202) based on, for example, one or more physiological parameters such as an elevated blood pressure. For example, the presence of elevated sympathetic tone may be determined or detected in various manners. For example, an elevated sympathetic tone may be determined based on one or more monitored physiological parameters of a patient (e.g., at least one physiological parameter) such as, for example, the electrical activity of the patient or patient's heart, the chemical activity of the patient or patient's heart, hemodynamic pressure of the patient, etc. At least in one embodiment, elevated sympathetic tone is determined based on elevated blood pressure (e.g., a patient determined to have hypertension).

For example, the electrical activity of a patient may include one or more signals that may be monitored (e.g., using electrodes from locations in or around the patient's heart, or other locations of the body, including outside of the body). Using such monitored electrical activity, certain metrics may be determined and collected (e.g., for analysis to determine a sustained condition, a temporary condition, etc.). For instance, the following metrics may be determined and collected using the electrical activity of the patient: heart rate (HR), heart rate variability (HRV), galvanic skin response (GSR), respiratory events including breathing or respiratory rate (e.g., using impedance measurements such as in impedance plethysmography), etc.

The chemical activity of a patient may include one or more chemical properties that may be monitored (e.g., using various sensors from locations in or around the patient's heart, or other locations of the body, including outside of the body). Using such monitored chemical activity, certain metrics may be determined and collected (e.g., for analysis to determine a sustained condition, a temporary condition, etc.). For instance, the following metrics may be determined and collected using the chemical activity of the patient's heart: oxygen saturation, lung fluid status, etc.

The hemodynamic activity of a patient may include one or more hemodynamic pressures that may be monitored (e.g., using various sensors from locations in or around the patient's heart or other locations of the body, and/or in or around (e.g., outside of) the patient's body). Using such monitored hemodynamic pressures of a patient, certain metrics may be determined and collected (e.g., for analysis to determine a sustained condition, a temporary condition, etc.). For instance, the following metrics may be determined and collected using the hemodynamic pressures of the patient (e.g., using an IMD 10 or other devices, such as, Medtronic OptiVol Fluid Status Monitoring devices): mean arterial pressure, diastolic blood pressure, systolic blood pressure, flow rates, pressure drops, pulmonary artery pressure, pulmonary capillary wedge pressure, right ventricular systolic pressure, right ventricular diastolic pressure, changes in oxygen saturation of the tissue or blood, changes in the amplitude or timing of heart sounds, changes in intrathoracic impedance, changes in intracardiac impedance, heart sounds, lung sounds, tissue perfusion, intracardiac pressure, pulmonary vein pressure, cardiac imaging, shear stress, partial pressure of oxygen, respiratory cycles (e.g., including respiratory events such as the start of the inspiration phase, end of inspiration phase, or other respiratory waveform events), etc.

The nerve activity of a patient may include one or more signals monitored (e.g., using electrodes/sensors at locations in or around the patient's heart or other locations of the body, and/or from locations proximate patient's nerves). More specifically, the electrical signals propagating along the one or more nerve fibers innervating musculature of a patient may include parasympathetic and sympathetic signals propagating along efferent and afferent nerve fibers. For instance, metrics may be determined and collected using the nerve activity monitoring, such as muscle sympathetic nerve activity (MSNA).

In other words, an elevated sympathetic tone may be determined based on one or more monitored physiological parameters of a patient (e.g., at least one physiological parameter). For example, the monitored physiological parameters may be indicative of an elevated sympathetic tone. For example, an elevated sympathetic tone may be determine based on the monitored one or more physiological parameters in comparison to thresholds or baselines provided or defined for a patient. For example, an elevated sympathetic tone may be determined based on an at least one of elevated blood pressure, an elevated heart rate, decreased heart rate variability, decreased muscle sympathetic nerve activity, a decreased galvanic skin response, and/or an increased respiratory rate. At least in one embodiment, elevated sympathetic tone is determined based on elevated blood pressure (e.g., a patient determined to have hypertension).

Upon a determination that an elevated sympathetic tone exists for a patient, a plurality of breathing therapy sessions are provided (block 204). Such breathing therapy sessions may be part of treatment plan (e.g., a scheduled plan, for example, defining a plurality of breathing sessions for a patient and carried out under control of the IMD 10).

In one or more embodiments, the plurality of breathing therapy sessions (block 204) may include use of diaphragm contraction prolongation. For example, the use of stimulation after the start of the inspiration phase of the breathing cycle to prolong diaphragm contraction during the breathing cycle.

One or more embodiments of providing such diaphragm contraction prolongation are described in U.S. Pat. App. Pub. No. US2007/0118183 to Gelfand et al., published May 24, 2007, and entitled "System and Method to Modulate Phrenic Nerve to Prevent Sleep Apnea," which describes treating breathing disorders such as central sleep apnea using stimulation provided to the phrenic nerve through a transvenous lead system. U.S. Pat. App. Pub. No. US2007/0118183 describes use of stimulation beginning after inspiration to extend the duration of a breath and to hold the diaphragm in a contracted condition (e.g., prolong diaphragm contraction).

In one or more embodiments to provide diaphragm contraction prolongation for breathing therapy as described herein, the respiratory cycle of a patient is monitored using one or more physiological parameters, such as impedance and/or pressure measurements. For example, respiratory monitoring is described in U.S. Pat. No. 7,623,917 to Cho et al., issued Nov. 24, 2009, entitled "Method of Optimizing Data Collection and Therapy Delivery Based on Respiration," which is incorporated herein in its entirety.

As described in U.S. Pat. No. 7,623,917, hemodynamic parameters may be used in accordance with various embodiments to monitor the respiratory cycle (e.g., determine breathing cycle events such as the start of the inspiration phase). For example, right ventricular pressure (RVP) and/or left ventricular pressure (LVP) acquired during respiration in a patient may be collected via pressure sensors (e.g., at sample rates as high as 256 Hz or higher) and respiration waveforms may be derived therefrom. For example, the RVP and/or LVP signals, respectively, may be passed through a low-pass filter (e.g., such that higher frequency components may be filtered out or removed) according to one or more embodiments. Further, for example, the respiratory cycle may be derived based on either RVP or LVP, or a combination thereof.

The respiratory cycle derived from the pressure measurements may be used to provide the two relatively distinct phases of the respiratory cycle, i.e., the inspiration phase and the expiration phase, as well as respiratory rate. Various phase events are present in a respiratory cycle, such as the start of the inspiration phase, the end of the inspiration phase, the start of the expiration phase, and the end of the expiration phase.

Further, it may be desirable to have multiple timing reference points defined within a given respiratory cycle, or within one or both of the inspiration and expiration phases. For example, it may be desirable to define the start or the end of the inspiration phase, and/or points in the respiratory cycle, such as for use in delivering stimulation at one or more times during the respiratory or breathing cycle.

Still further, for example, the respiratory cycle may be derived from impedance measurements made using multiple electrodes (e.g., an electrode on a lead and a can electrode provided as part of the IMD 10). For example, an electrode on a lead may cooperate with an indifferent electrode on the can of the IMD 10 to source and sink low amplitude electrical pulses that are used to track changes in lung volume over time (e.g., based on impedance). This may be referred to as impedance plethysmography and may also be used to derive the inspiration and expiration events of an individual breath, as well as to track breathing rate.

Still further, other types of respiration sensing may also be used. For example, a sensor for measuring chest movement (e.g., a sensor outside the patient's body) such as with a respiration belt may be used, or a thermistor based system may be used. Impedance type respiratory tracking, pressure based respiratory tracking, or any other respiratory tracking process, may be used alone or in combination to derive the respiratory or breathing cycle. Such processes can measure the respiration of the patient and the resulting respiration data may be collected over periods of time (e.g., data over minutes, hours, and days can be logged), transmitted, and/or used to direct the breathing therapy.

With the respiratory cycle of a patient derived, stimulation may be timed to provide for diaphragm contraction prolongation. For example, when a breathing therapy session is implemented over a plurality of breathing cycles, stimulation is used to prolong diaphragm contraction. For example, the stimulation (e.g., of the phrenic nerve) may occur at a time after the beginning or start of the inspiration phase. In one or more embodiments, the stimulation may begin after the onset of exhalation or expiration. Any suitable shape of stimulation pulse and/or amplitude thereof may be used to provide the stimulation. However, when delivered, stimulation is provided such that the stimulation "stills" the diaphragm resulting in an amount of air trapped in at least one lung and extends the breath duration. In other words, suitable stimulation initiated after inspiration can "prolong" or "hold" the breath, and thus regulate breathing.

With further reference to FIG. 4, the plurality of breathing therapy sessions may be provided in one or more different manners. For example, in one or more embodiments, breathing therapy sessions may be activated one or more times a day (i.e., 24 hour period) with a predetermined duration (e.g., minutes, hours, etc.). Further, for example, in one or more embodiments, one or more breathing therapy sessions may be activated during each of one or more days.

Such breathing therapy sessions may be of any number and each of such breathing sessions may be of any duration. In other words, the type of breathing sessions used to train an individual to breath slower will, at least in part, be determined on a patient by patient basis. For example, a patient with a temporary elevated sympathetic tone may be scheduled with different breathing therapy sessions than a person with a chronic sustained condition. For example, a 30 minute session, once a day for several weeks, may be effective for a patient with a temporary elevated sympathetic tone, whereas, 2 to 3 breathing therapy sessions per day for months may be needed to provide an effect in a patient with a sustained or chronic elevated sympathetic tone.

In one or more embodiments, the breathing therapy sessions are scheduled and/or carried out when a patient is not cognitive of respiratory control (e.g., when the patient is breathing autonomously). For example, breathing therapy sessions may be carried out with a patient, such as a quadraplegic patient (e.g., who has lost respiratory sensation and is not cognitive of respiratory control), for the purpose of attempting to train the patient to control breathing (e.g., such sessions may be carried out when the patient is awake). Further, in one or more embodiments, the breathing therapy sessions may be carried out when a patient is asleep and is not cognizant of their respiratory control.

Figure 7:
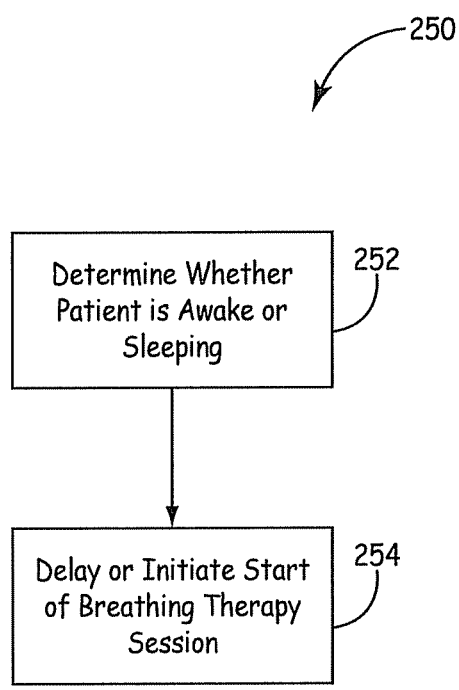
FIG. 7 is a flow chart depicting an exemplary process that may be used in combination with, for example, the breathing therapy processes described herein.

As shown in FIG. 7, an activity detection method 250 may be used in combination with one or more breathing therapy processes described herein (e.g., breathing therapy process 200 as shown generally in FIG. 4). For example, the method 250 may include determining whether the patient is awake or sleeping (e.g., a substantially reduced level of activity) (block 252) prior to activating a breathing therapy session. Such a determination may be implemented with the use of an activity sensor (e.g., an accelerometer), posture sensor, etc. For example, if the patient exhibits a higher level of activity (e.g., relative to a baseline or threshold), activation of a breathing therapy session may be delayed (block 254). Further, for example, if the patient exhibits a lower level of activity (e.g., relative to a baseline or threshold, or indicative of a sleeping state), a breathing therapy session may be activated (block 254).

In one or more embodiments, for example, a breathing therapy session may be scheduled to be carried out during a particular time. If it is determined that the patient is awake during this particular scheduled time, then the breathing therapy session may be delay (e.g., the schedule may be adjusted, activity level may be checked continuously over a period of time until the therapy session may be activated, etc.). Further, in one or more embodiments, for example, a breathing therapy session may be activated upon a determination that the patient is asleep (e.g., each day, when a person is first determined to be asleep, a breathing therapy session is activated).

The breathing therapy method 200 of FIG. 4 may be implemented as an open loop control process. For example, upon a determination that a patient exhibits elevated sympathetic tone (block 202) (e.g., exhibits hypertension or high blood pressure), a breathing therapy may be defined for the patient. For example, a pre-programmed breathing therapy protocol may be implemented for the patient (e.g., carried out by the IMD 10) using respiratory sensing to time stimulation. For example, one or more breathing therapy sessions per day may be scheduled with such sessions each being carried out for a predetermined period of time (e.g., one session a day for 30-60 minutes). One will recognize that such a session may be delayed depending on a determination of whether the patient is asleep when the session is scheduled. In other words, the pre-programmed diaphragm contraction prolongation protocol (e.g., over a plurality of breathing therapy sessions) may be carried out regulate the breathing pattern of the patient (e.g., to train the patient to breath slower over time).

Figure 5:
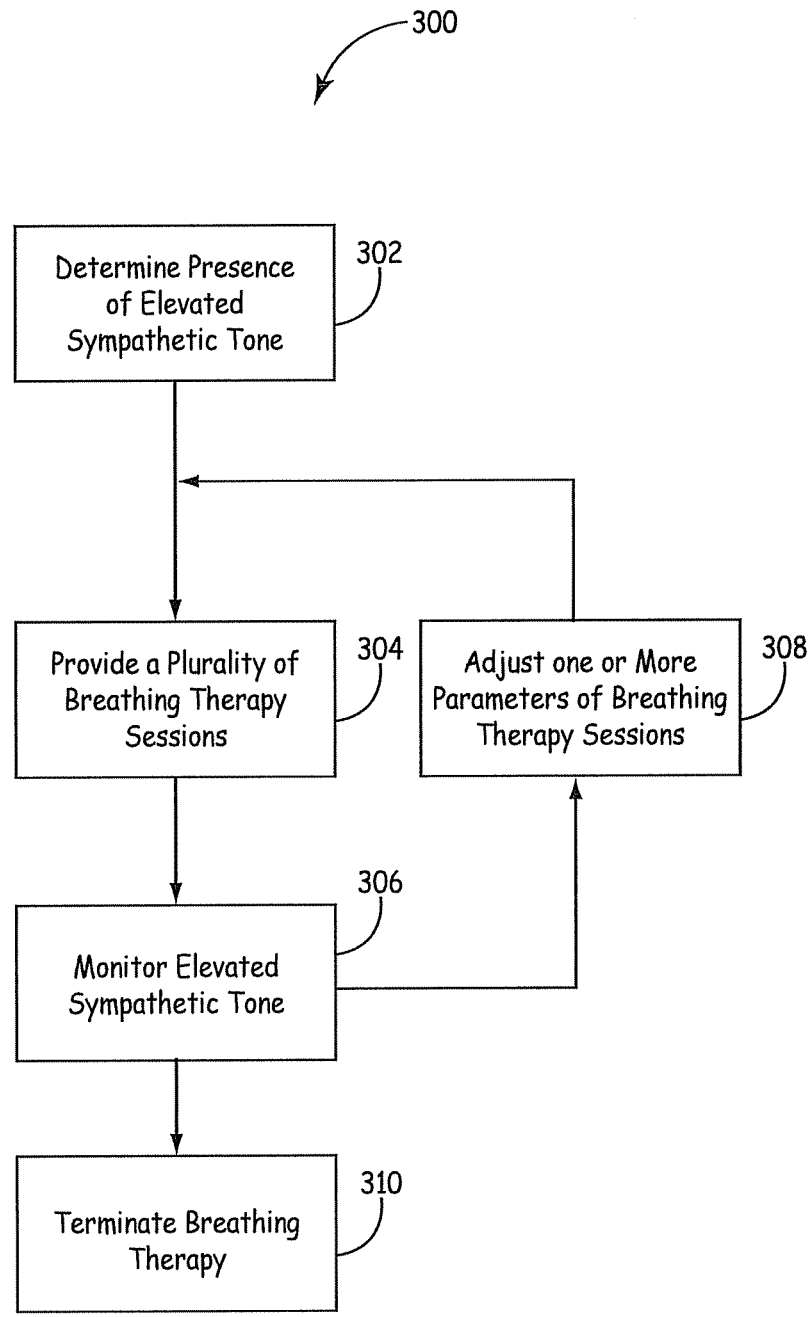
FIG. 5 is a flow chart depicting an exemplary method of providing breathing therapy, e.g., using diaphragm contraction prolongation, such as shown generally in FIG. 4.

Further, in one or more embodiments, breathing therapy may be implemented as a closed loop control process as shown by the breathing therapy method 300 of FIG. 5. For example, upon a determination that a patient exhibits elevated sympathetic tone (block 302), a breathing therapy may be defined for the patient which may include a plurality of breathing sessions 304 to be carried out. For example, a breathing therapy protocol may be implemented for the patient (e.g., to be carried out by the IMD 10) using respiratory sensing to time stimulation.

However, unlike the open loop process, one or more physiological parameters of a patient are monitored to determine a change in the elevated sympathetic tone and one or more characteristics of one or more breathing therapy sessions may be adjusted based thereon. For example, the physiological parameters used to determine that a patient exhibits an elevated sympathetic tone, or any other patient physiological parameters, may be monitored (block 306) and used as feedback to adjust one or more parameters of the plurality of breathing sessions (block 308) (e.g., such that therapy is continued and adjusted until a defined target for one or more of the physiological parameters is reached). For example, the number of breathing therapy sessions per day may be changed, the duration of such sessions may be changed, additional breathing therapy sessions may be scheduled and/or carried out, target breathing cycle lengths may be adjusted, etc. Further, for example, once the defined target level for one or more the physiological parameters (e.g., such as those used to determine an elevated sympathetic tone for the patient, or any other patient parameters) being monitored (block 306) has been reached, the breathing therapy may be terminated (block 310).

For example, in one embodiment, blood pressure (e.g., indicative of hypertension) may be used to determine an elevated sympathetic tone for a patient (e.g., the blood pressure may be elevated relative to a baseline or target pressure). In such a case, in the closed loop system, blood pressure may continuously be monitored to determine a change therein. Such monitoring of the blood pressure may be used as feedback for adjusting one or more characteristics of one or more breathing therapy sessions (e.g., until a defined target blood pressure is reached).

It will be recognized that such monitoring of one or more physiological parameters of a patient may be used as feedback between breathing therapy sessions (e.g., to modify one or more parameters of a subsequent breathing therapy session) or within a breathing therapy session (e.g., to modify one or more parameters of a session currently being carried out).

Figure 6:
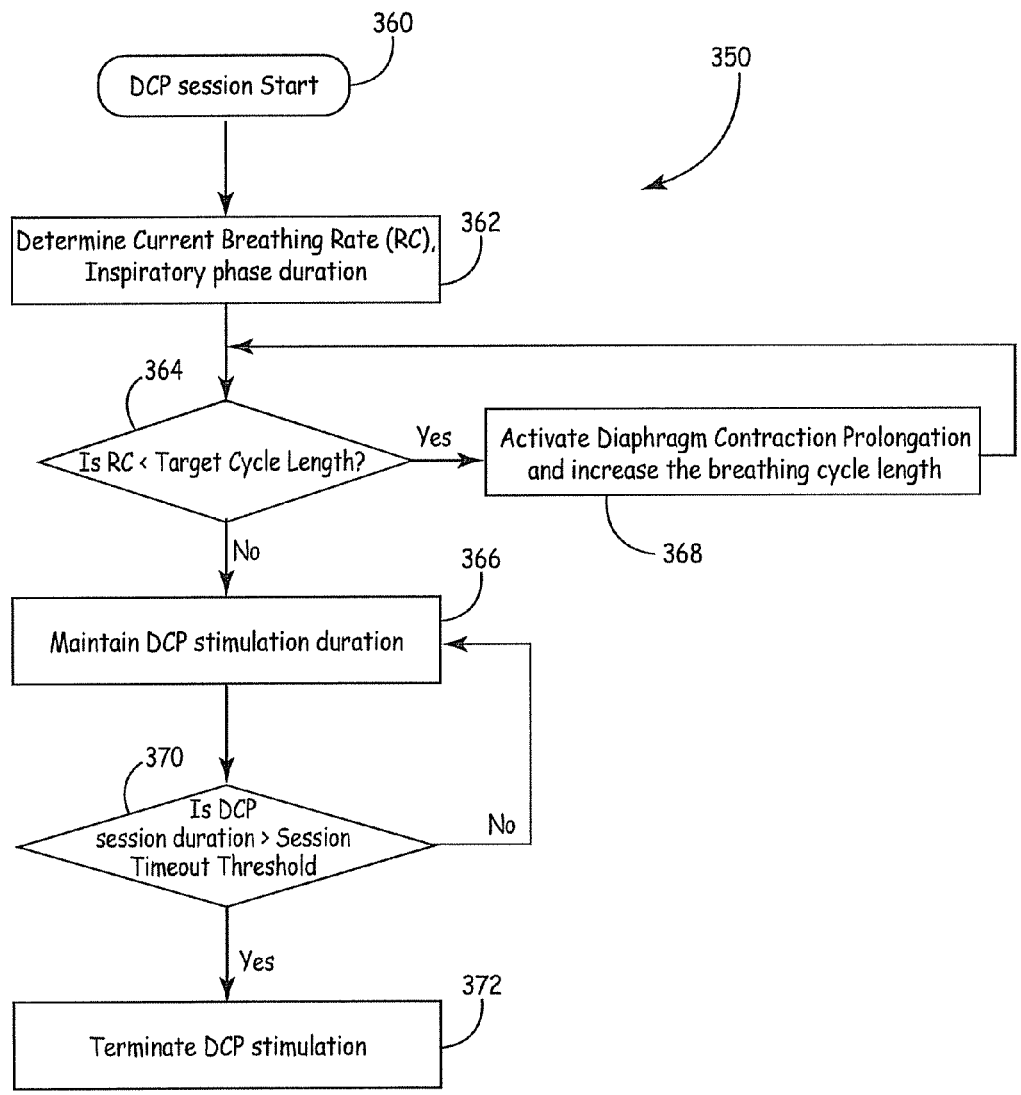
FIG. 6 is a flow chart depicting an exemplary breathing therapy session, e.g., using diaphragm contraction prolongation, that may be used in the breathing therapy processes such as shown in FIGS. 4-5.

In one or more embodiments, a breathing therapy session may be implemented as shown by the method 350 of FIG. 6. For example, each of the plurality of breathing therapy sessions or diaphragm contraction prolongation (DCP) therapy sessions may include determining a current breathing cycle length for the patient (e.g., derived from the current breathing rate) and a duration of the inspiration phase of a current breathing cycle (block 362) upon activation of the session (block 360). With a target cycle length being set for the patient (e.g., predefined, defined based on current breathing cycle length, etc.), the current breathing rate is monitored (e.g., current breathing rate detected is compared to the target breathing rate) (block 364) and stimulation delivered to prolong diaphragm contraction to increase the breathing rate cycle length until the target cycle length is attained (e.g., delivering stimulation after the start of the inspiration phase of each of a plurality of breathing cycles to provide an increasing diaphragm contraction prolongation over the plurality of breathing cycles until the target breathing cycle length of the patient is attained) (block 368). For example, the duration of the stimulation delivered over the plurality of breathing cycles may follow an increasing linear function to provide an increasing breathing cycle length.

Once the current breathing cycle length is equal to the target cycle length (block 364), then stimulation is continued to maintain the target breathing cycle length of the patient (e.g., after the target breathing cycle length is attained, the stimulation amplitude or duration which allowed the patient to attain the target breathing length is maintained) (block 366). It is noted that if the current breathing rate should fall below the target breathing rate during attempts to maintain the target, the process shown by blocks 364, 368 may be repeated to get back to the target breathing rate. Further, for example, stimulation after the target breathing cycle length of the patient is attained may be continued until the end of the predefined time period for the breathing therapy session (block 370). In other words, if the duration of the current breathing therapy session is less than a session timeout threshold (block 370) (e.g., the predetermined time for the session has not yet expired), then stimulation to maintain the target breathing cycle length is continued (block 366). However, if the duration of the current breathing therapy session is equal to the session timeout threshold (block 370), then stimulation for this session is terminated (block 372).

For example, the diaphragm contraction prolongation (DCP) sessions or breathing therapy sessions may be activated one or more times during the day (i.e., 24 hours) and continued for a predetermined duration (e.g., 15-30 minutes). During the breathing therapy session, one or more respiration sensors (e.g., impedance, pressure, chest movement, etc.) may be employed to monitor respiration phases, rate, and tidal volume. For example, when the breathing rate is higher than a predetermined threshold (e.g. 8 cycles/min or 7.5 sec/cycle) which may be indicative of an elevated sympathetic tone, one or more breathing therapy sessions may be implemented, e.g., using stimulation to provide diaphragm contraction prolongation, such as stimulation applied after the start of the inspiration phase and 50-100 ms before the estimated termination of inspiration phase.

For example, to carry out the stimulation, the inspiration phase of the respiratory cycle may be estimated based on the mean value of prior breathing cycles (e.g., three prior breathing cycles or in some other programmable manner). The estimated inspiration phase may then be used to time the stimulation. For example, the duration of the DCP stimulation can follow a linear function to increase the breathing cycle. In other words, in one exemplary embodiment, for example, if the breathing cycle length is 4 seconds, inspiration phase is 2 seconds, and the target cycle length is 7.5 seconds, then DCP duration, $Y(t)=mX(t)+b$, where $X(t)$ is the inspiration phase length at time t, and m (m<1), b are programmable parameters, is increased until the breathing cycle length reaches its target value of 7.5 seconds. Once the current breathing cycle length reaches the target value, $Y(t)$ is constant as long as the cycle length does not change by a preset tolerance boundary (+/−10%) until the breathing therapy session duration expires.

One will recognize that the duration or other parameters of the stimulation may follow some other function besides a linear function to increase breathing cycle length. For example, such stimulation may use a larger increase in stimulation duration early in the breathing therapy session as opposed to later in the session (e.g., a non-linear function), such stimulation may be adjusted in amplitude to achieve an increase in breathing rate, etc. Stimulation waveforms may be varied in amplitude and duration to adjust therapy. Further, the time of application of the stimulation within the breathing cycle may also be adjusted to control prolongation.

Figure 8:
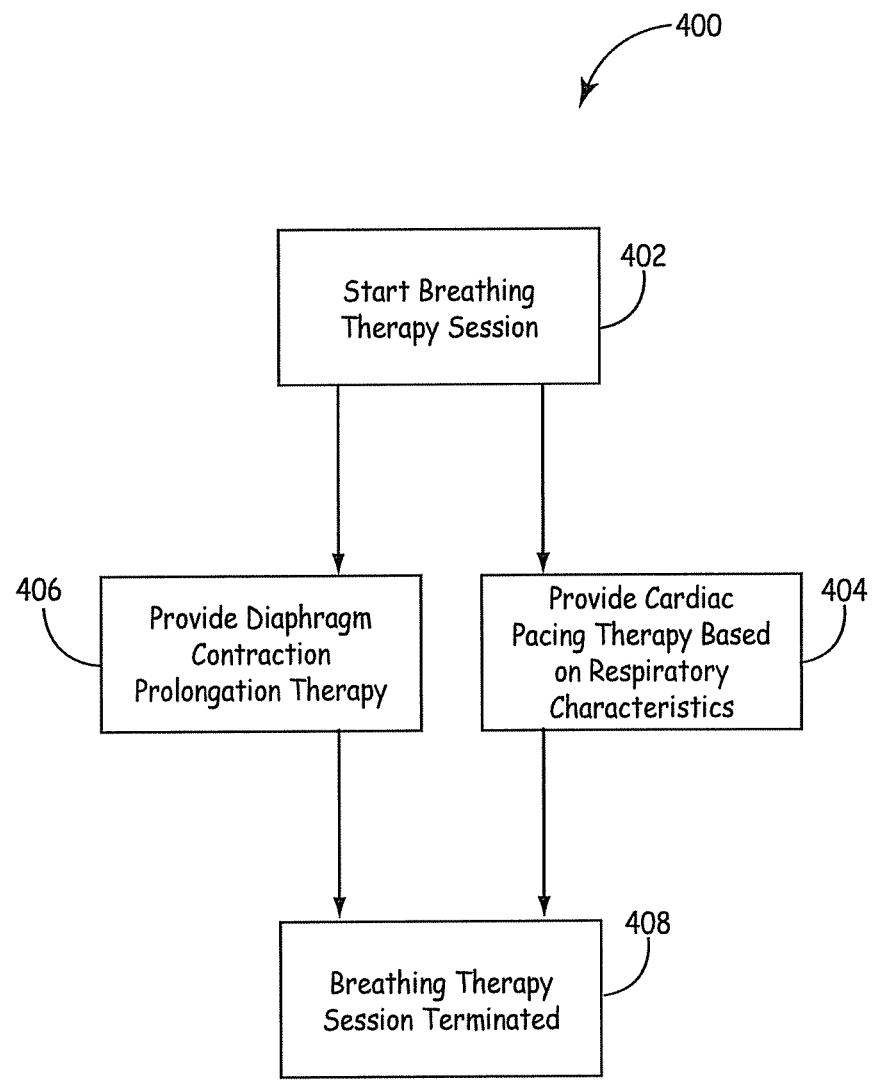
FIG. 8 is a flow chart depicting an exemplary process that shows use of cardiac pacing therapy in combination with, for example, the breathing therapy processes (e.g., using diaphragm contraction prolongation) such as shown in FIGS. 4-6.

Further, in one or more embodiments, a breathing therapy session may be implemented as shown by the method 400 of FIG. 8 wherein pacing therapy based on one or more respiratory characteristics may be used (block 404) in combination with diaphragm contraction prolongation therapy (406) during an initiated breathing therapy session (block 404). Such pacing therapy may be used during a part of the session, throughout the entire session, periodically during the session, etc., or until the breathing therapy session is terminated (block 408). For example, such pacing and breathing therapy may be implemented using an IMD generally shown herein with reference to FIGS. 1-3 and/or an IMD 90 as shown and described with reference to FIG. 9. Such a combination therapy may, for example, provide benefits for patients with chronotropic incompetence (e.g., the inability of the heart to increase its rate with increased activity), or any other patients with an elevated sympathetic tone.

Figure 9:
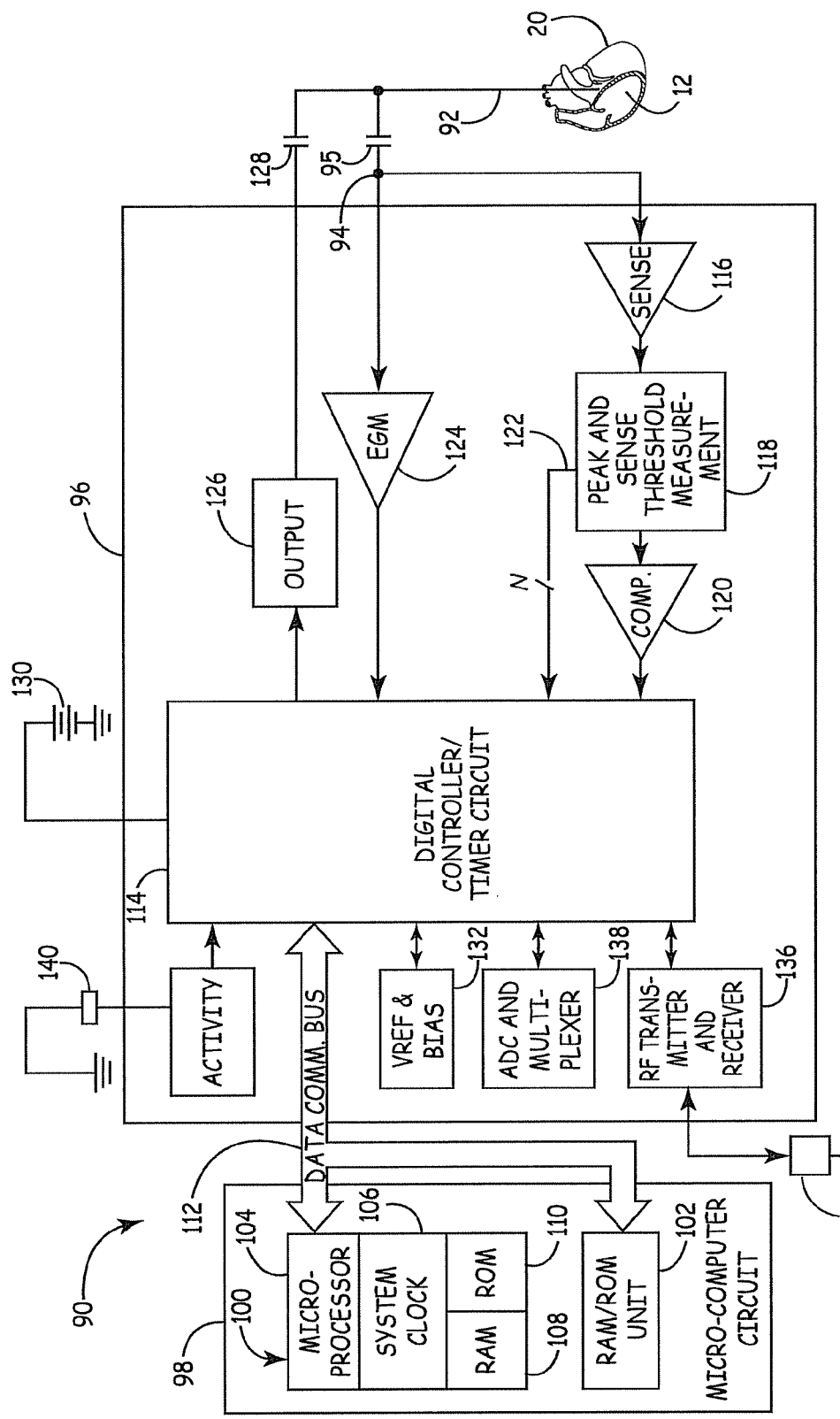
FIG. 9 is a schematic diagram illustrating another embodiment of an exemplary implantable medical device (IMD) operably coupled to a patient's heart.

For example, FIG. 9 is a block diagram illustrating constituent components of the exemplary IMD 90. DAD 90 may be a pacemaker having a microprocessor-based architecture. For the sake of convenience, IMD 90 in FIG. 9 is shown with only a single lead 92 connected thereto. IMD 90 may include any number of leads 92 to which similar circuitry and connections not explicitly shown in FIG. 9 may apply. For example, in one embodiment, leads 92 may correspond to leads 16 of FIGS. 1-2.

As shown in FIG. 9, lead(s) 92 are coupled to node 94 in IMD 90 through input capacitor 95. Input/output circuits 96 contain analog circuits for interfacing to lead 92 and circuits for the application of stimulation to one or both of phrenic nerves 14 and, in some embodiments, the heart 20 of patient 12. The delivery of stimulation to phrenic nerves 14 may be controlled by software-implemented algorithms stored within microcomputer circuit 98. In embodiments where IMD 90 is also used to pace heart 20, software-implemented algorithms stored within microcomputer circuit 98 may also control the rate of heart 20.

Microcomputer circuit 98 preferably comprises on-board circuit 100 and off-board circuit 102. On-board circuit 100 preferably includes microprocessor 104, system clock circuit 106 and on-board RAM 108 and ROM 110. Off-board circuit 102 preferably comprises a RAM/ROM unit. On-board circuit 100 and off-board circuit 102 are each coupled by data communication bus 112 to digital controller/timer circuit 114. Microcomputer circuit 98 may comprise a custom integrated circuit device augmented by standard RAM/ROM components.

Operating commands for controlling the delivery of stimulation by IMD 90 are coupled by data bus 112 to digital controller/timer circuit 114. For example, software-implemented algorithms stored within microcomputer circuit 98 may cause processor 104 to direct digital controller/timer circuit 114 via data bus 112 to cause the stimulation of phrenic nerves 14 in response to a signal indicating activation of breathing therapy. Where IMD 90 is used to pace heart 20, digital timers and counters of digital controller/timer circuit 114 establish the overall escape interval of the IMD 90, as well as various refractory, blanking and other timing windows for controlling the operation of peripheral components disposed within input/output circuits 96.

Digital controller/timer circuit 114 may be coupled to sensing circuitry, including sense amplifier 116, peak sense and threshold measurement unit 118 and comparator/threshold detector 120. Circuit 114 may also be coupled to electrogram (EGM) amplifier 124 for receiving amplified and processed signals sensed by lead 92. The electrogram signal provided by EGM amplifier 124 is employed when IMD 90 is being interrogated by an external programmer to transmit a representation of a cardiac analog electrogram. The electrogram signal may also be converted to a digital signal by ADC and multiplexer circuit 138 and provided microcomputer circuit 98 for digital signal analysis by microprocessor 104, which may, for example, analyze the signal for one or more purposes.

Sense amplifier 116 amplifies sensed electrical cardiac signals and provides an amplified signal to peak sense and threshold measurement circuitry 118, which in turn provides an indication of peak sensed voltages and measured sense amplifier threshold voltages on multiple conductor signal path 122 to digital controller/timer circuit 114. An amplified sense amplifier signal is then provided to comparator/threshold detector 120. Sense amplifier 116, peak sense and threshold measurement unit 118 and comparator/threshold detector 120 may be used by circuit 114 to detect intrinsic events within heart 20, such as depolarizations or repolarization of atria or ventricles.

Output pulse generator 126 provides stimulation to phrenic nerves 14 through coupling capacitor 128 in response to signals provided by digital controller/timer circuit 114. Signals provided by digital controller/timer circuit 114 may control the amplitude, and other characteristics of the phrenic stimulation. High amplitude pulses may be provided by output pulse generator 126 in order to ensure capture of phrenic nerves 14 and adequate contraction prolongation of diaphragm 18.

Digital controller/timer circuit 114 may also control the timing of stimulation of phrenic nerves 14, as well as cardiac pacing pulses. Circuit 114 may cause output pulse generator to deliver stimulation based on detected respiratory and/or intrinsic cardiac events. Where IMD 90 also paces heart 20 via output pulse generator 126, output pulse generator 126 may provide pacing stimuli to heart 20 through coupling capacitor 98 in response to a pacing trigger signal provided by digital controller/timer circuit 114 each time the escape interval times out, an externally transmitted pacing command is received or in response to other stored commands as is well known in the pacing art. Circuit 114 may direct output pulse generator 126 to increase the amplitude of pacing pulses in order to stimulate phrenic nerves 14, as described above. In some embodiments, IMD 90 may include separate leads 92, sensing circuitry 116-120, and output pulse generators 126 for cardiac pacing, and leads 92 and output pulse generators 126 for delivering stimulation to phrenic nerves 14.

Electrical components shown in FIG. 9 are powered by an appropriate implantable battery power source 130 in accordance with common practice in the art. For the sake of clarity, the coupling of battery power to the various components of IMD 90 is not shown in the FIG. 9. VREF and Bias circuit 132 most preferably generates stable voltage reference and bias currents for analog circuits included in input/output circuit 96.

Antenna 134 is connected to input/output circuit 96 to permit uplink/downlink telemetry through RF transmitter and receiver telemetry unit 136. Telemetry unit 136 may receive a signal indicating a need for breathing therapy from patient activator 32 (FIG. 1) via antenna 134. Further, IMD 90 may be programmable by means of an external programming unit (not shown) via antenna 134 and telemetry unit 136.

IMD 90 may include activity sensor or accelerometer 140. Activity sensor 140 typically (although not necessarily) provides a sensor output that varies as a function of a measured parameter relating to a patient's metabolic requirements. The output signal provided by activity sensor 140 is coupled to input/output circuit 96. Microprocessor 104 may receive the output signal provided by activity sensor 140, and determine whether a person is inactive (e.g., asleep). For example, microprocessor 104 may compare the output signal to one or more threshold values stored in one of memories 102, 108 and 110.

Although FIG. 9 is a block diagram illustrating constituent components of a pacemaker, it will be recognized that a pacemaker-cardioverter-defibrillator (PCD) having a microprocessor-based architecture may also be used to carry out breathing therapy (e.g., including DCP and cardiac pacing), along with carrying out additional functionality typically provided by a PCD.

Where IMD 90 is used to pace heart 20, circuit 114 may include programmable digital counters which control the basic time intervals associated with DDD, VVI, DVI, VDD, AAI, DDI and other modes of single, dual and three chamber pacing well known to the art. For example, circuit 114 may control the time intervals associated with biventricular cardiac resynchronization therapy. Circuit 114 may also control escape intervals associated with anti-tachyarrhythmia pacing in right atrium 24, right ventricle 26, and/or left ventricle 28, employing any anti-tachyarrhythmia pacing therapies known to the art.

In further reference to FIG. 8, the cardiac pacing used during breathing therapy sessions (block 404) along with diaphragm contraction prolongation therapy (block 406) may be delivered in various manners. Such cardiac pacing may include atrial, ventricular or bi-ventricular pacing, to mimic the respiratory sinus arrhythmia.

In one or more embodiments, for example, cardiac pacing may be delivered to the patient based on a predefined ratio of breathing rate to heart rate. For example, a set of predefined ratios may be used to pace the heart during delivery of diaphragm contraction prolongation therapy as the breathing cycle length is increased, or maintained at a target length. For example, such ratios of breathing rate to heart rate ratios may include 1:4, 1:5, 1:6, etc. In other words, for example, the heart may be paced to accomplish 5 beats per breath, 6 beats per breath, etc.

Further, in one or more embodiments, for example, cardiac pacing may be delivered to the patient based on a predefined ratio of inspiration pacing rate to expiration pacing rate. For example, a set of predefined ratios may be used to pace the heart during delivery of diaphragm contraction prolongation therapy as the breathing cycle length is increased, or maintained at a target length. For example, such ratios of inspiration pacing rate to expiration pacing rate may include 3:1; 3:2, 2:1, etc. In other words, for example, if the heart is to be paced at 8 beats per breath, the heart may be paced to accomplish 6 beats within the expiration phase and 2 beats in the inspiration phase when the ratio of 3:1 is used to control such pacing.

Figure 10:
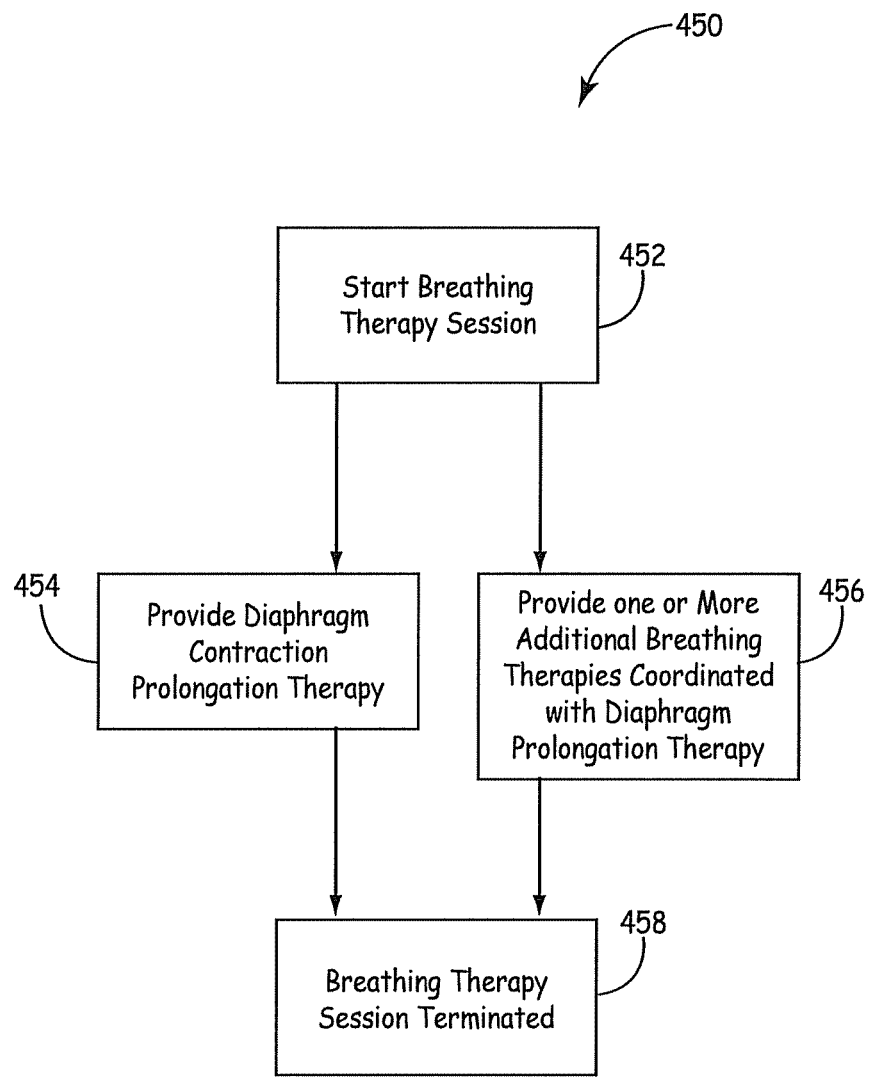
FIG. 10 is a flow chart depicting an exemplary process that shows use of other breathing therapies in combination with, for example, the breathing therapy processes (e.g., using diaphragm contraction prolongation) such as shown in FIGS. 4-6.

Still further, for example, as shown by method 450 in FIG. 10, one or more additional breathing therapies may be used (block 456) in combination with diaphragm contraction prolongation (block 454) during an initiated breathing session (block 452). Such therapies may be used during a part of the session, throughout the entire session, periodically during the session, etc., or until the breathing therapy session is terminated (block 458). For example, such therapies may be implemented as described herein with reference to FIG. 1. For example, such additional therapies may include providing at least one of carotid sinus stimulation, aortic baroreceptor stimulation, baroreflex activation therapy, vagus nerve stimulation, spinal cord stimulation, renal nerve block, and drug therapy.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A medical device for providing breathing therapy comprising:
   monitoring apparatus configured to monitor one or more physiological parameters of a patient;
   a therapy delivery module configured to deliver electrical stimulation to a patient in which the presence of a temporary or sustained elevated sympathetic tone has been determined, wherein the elevated sympathetic tone is determined based at least on an elevated blood pressure; and
   a control module configured to:
      determine at least the inspiration phase of one or more breathing cycles based on the monitored physiological parameters; and
      control delivery of a plurality of breathing therapy sessions, wherein each of the breathing therapy sessions is provided during a defined time period, and further wherein each of the plurality of breathing therapy sessions comprises delivering stimulation after the start of the inspiration phase of each of a plurality of breathing cycles to prolong diaphragm contraction during the breathing cycle,
   wherein the therapy module is further configured for delivering cardiac stimulation, wherein the control module is configured to control delivery of cardiac pacing to the patient based on predefined ratios of breathing rate to heart rate.

2. The device of claim 1, wherein the control module is further configured to determine the presence of the elevated sympathetic tone of a patient based on the monitored one or more physiological parameters of a patient.

3. The device of claim 1, wherein the therapy delivery module is configured to deliver at least one of phrenic nerve stimulation, diaphragmatic stimulation, intercostals muscle stimulation, and central respiratory control center stimulation.

4. The device of claim 1, wherein the therapy delivery module is configured to deliver phrenic nerve stimulation.

5. The device of claim 1, wherein the control module is further configured to provide one or more breathing therapy sessions during each of a plurality of days.

6. The device of claim 1, wherein the control module is further configured to:
   determine a current breathing cycle length for the patient and duration of the inspiration phase of the current breathing cycle;
   provide a target breathing cycle length for the patient; and
   control delivery of stimulation after the start of the inspiration phase of each of a plurality of breathing cycles and prior to termination of the inspiration phase of such breathing cycles to provide an increasing diaphragm contraction prolongation over the plurality of breathing cycles until the target breathing cycle length of the patient is attained.

7. The device of claim 6, wherein the control module is further configured to control delivery of stimulation such that the duration and/or amplitude of the stimulation delivered over the plurality of breathing cycles follows an increasing linear function.

8. The device of claim 6, wherein the control module is further configured to control delivery of stimulation such that, during each of the plurality of breathing therapy sessions, stimulation is continued after the target breathing cycle length of the patient is attained to maintain the target breathing cycle length of the patient until the end of the predefined time period for the breathing therapy session.

9. The device of claim 1, wherein the control module is configured to control delivery of cardiac pacing to the patient based on a predefined ratio of inspiration pacing rate to expiration pacing rate.

10. The device of claim 1, wherein the control module is configured to determine when a patient is sleeping, and further configured to provide the plurality of breathing therapy sessions when the patient is sleeping.

11. The device of claim 1, wherein the control module is configured to determine the presence of an elevated sympathetic tone based on at least one of determining the presence of at least one of an elevated blood pressure, an elevated heart rate, a decreased heart rate variability, decreased muscle sympathetic nerve activity, a decreased galvanic skin response, and an increased respiratory rate.

12. The device of claim 1, wherein the control module is configured to determine a change in the elevated sympathetic tone and configured to adjust one or more parameters of one or more breathing therapy sessions based thereon.

13. The device of claim 12, wherein the control module is configured to determine a change in at least blood pressure of the patient to determine a change in the elevated sympathetic tone and is configured to adjust one or more parameters of one or more breathing therapy sessions based thereon.

14. The device of claim 1, wherein the control module is further configured to define a schedule to provide the plurality of breathing therapy sessions, and further wherein each of the breathing therapy sessions is provided during the defined time period such that a patient attains a target breathing cycle length during the breathing therapy session.

15. The device of claim 1, wherein the device is configured to operate in combination with one or more additional therapy apparatus configured to provide delivery of one or more additional therapies during each of the plurality of breathing therapy sessions, wherein the one or more additional therapies comprise at least one of carotid sinus stimulation, aortic baroreceptor stimulation, baroreflex activation therapy, vagus nerve stimulation, cardiac synchronization therapy, cardiac pacing, spinal cord stimulation, renal nerve block, and drug therapy.

16. A method for providing breathing therapy, comprising:
monitoring one or more physiological parameters of a patient to determine the presence of a temporary or sustained elevated sympathetic tone based on at least an elevated blood pressure;
monitoring respiration of a patient to determine at least the inspiration phase of one or more breathing cycles; and
providing a plurality of breathing therapy sessions upon determination of the presence of an elevated sympathetic tone, wherein each of the breathing therapy sessions is provided during a defined time period, and further wherein each of the plurality of breathing therapy sessions comprises delivering stimulation after the start of the inspiration phase of each of a plurality of breathing cycles to prolong diaphragm contraction during the breathing cycle,
wherein each of the plurality of breathing therapy sessions further comprises delivering cardiac pacing to the patient based on a predefined ratio of breathing rate to heart rate.

17. The method of claim 16, wherein delivering stimulation comprises delivering at least one of phrenic nerve stimulation, diaphragmatic stimulation, intercostal muscle stimulation, and central respiratory control center stimulation to control the breathing cycle of the patient.

18. The method of claim 16, wherein delivering stimulation comprises delivering phrenic nerve stimulation after the start of the inspiration phase of each of a plurality of breathing cycles and prior to termination of the inspiration phase of such breathing cycles to prolong diaphragm contraction during the breathing cycle.

19. The method of claim 16, wherein providing the plurality of one or more breathing therapy sessions comprises providing one or more breathing therapy sessions during each of a plurality of days.

20. The method of claim 16, wherein each of the plurality of breathing therapy sessions comprises:
determining a current breathing cycle length for the patient and duration of the inspiration phase of the current breathing cycle;
setting a target breathing cycle length for the patient;
delivering stimulation after the start of the inspiration phase of each of a plurality of breathing cycles and prior to termination of the inspiration phase of such breathing cycles to provide an increasing diaphragm contraction prolongation over the plurality of breathing cycles until the target breathing cycle length of the patient is attained.

21. The method of claim 20, wherein the duration and/or amplitude of the stimulation delivered over the plurality of breathing cycles follows an increasing linear function.

22. The method of claim 20, wherein each of the plurality of breathing therapy sessions further comprises continuing stimulation after the target breathing cycle length of the patient is attained to maintain the target breathing cycle length of the patient until the end of the predefined time period for the breathing therapy session.

23. The method of claim 16, wherein each of the plurality of breathing therapy sessions further comprises delivering cardiac pacing to the patient based on a predefined ratio of inspiration pacing rate to expiration pacing rate.

24. The method of claim 16, wherein the method further comprises providing the plurality of breathing therapy sessions when the patient is not cognitive of respiratory control.

25. The method of claim 24, wherein the method further comprises determining when the patient is sleeping, and further wherein the plurality of breathing therapy sessions are provided when the patient is sleeping.

26. The method of claim 16, wherein monitoring one or more physiological parameters of a patient to determine the presence of an elevated sympathetic tone comprises determining the presence of at least one of an elevated blood pressure, an elevated heart rate, a decreased heart rate variability, decreased muscle sympathetic nerve activity, a decreased galvanic skin response, and an increased respiratory rate.

27. The method of claim 16, wherein the method further comprises monitoring the one or more physiological parameters of a patient to determine a change in the elevated sympathetic tone and adjusting one or more characteristics of one or more breathing therapy sessions based thereon.

28. The method of claim 27, wherein the method comprises monitoring at least blood pressure of the patient to determine a change in the elevated sympathetic tone and adjusting one or more characteristics of one or more breathing therapy sessions based thereon.

29. The method of claim 16, wherein the method further comprises defining a schedule to provide the plurality of breathing therapy sessions, wherein each of the breathing therapy sessions is provided during the defined time period such that a patient attains a target breathing cycle length during the breathing therapy session.

30. The method of claim 16, wherein providing a plurality of breathing therapy sessions further comprises delivering one or more additional therapies during each of the plurality of breathing therapy sessions, wherein the one or more additional therapies comprise at least one of carotid sinus stimulation, aortic baroreceptor stimulation, baroreflex activation therapy, vagus nerve stimulation, cardiac synchronization therapy, cardiac pacing, spinal cord stimulation, renal nerve block, and drug therapy.

31. A medical device for providing breathing therapy comprising:
   means for monitoring one or more physiological parameters of a patient to determine the presence of a temporary or sustained elevated sympathetic tone based on at least an elevated blood pressure;
   means for monitoring respiration of a patient to determine at least the inspiration phase of one or more breathing cycles; and
   means for providing a plurality of breathing therapy sessions upon determination of the presence of an elevated sympathetic tone, wherein each of the breathing therapy sessions is provided during a defined time period, and further wherein each of the plurality of breathing therapy sessions comprises delivering stimulation after the start of the inspiration phase of each of a plurality of breathing cycles to prolong diaphragm contraction during the breathing cycle,
   wherein each of the plurality of breathing therapy sessions further comprises delivering cardiac pacing to the patient based on a predefined ratio of breathing rate to heart rate.

* * * * *